US012575796B2

(12) United States Patent
Smith et al.

(10) Patent No.: US 12,575,796 B2
(45) Date of Patent: Mar. 17, 2026

(54) SYSTEMS, DEVICES, AND METHODS FOR DETECTING BRAIN CONDITIONS FROM CRANIAL MOVEMENT DUE TO BLOOD FLOW IN THE BRAIN

(71) Applicant: The Regents of the University of California, Oakland, CA (US)

(72) Inventors: Wade Smith, San Francisco, CA (US); Paul Lovoi, Los Altos, CA (US)

(73) Assignee: The Regents of the University of California, Oakland, CA (US)

( * ) Notice: Subject to any disclaimer, the term of this patent is extended or adjusted under 35 U.S.C. 154(b) by 991 days.

(21) Appl. No.: 17/423,281

(22) PCT Filed: Jan. 16, 2020

(86) PCT No.: PCT/US2020/013947
§ 371 (c)(1),
(2) Date: Jul. 15, 2021

(87) PCT Pub. No.: WO2020/150521
PCT Pub. Date: Jul. 23, 2020

(65) Prior Publication Data
US 2022/0125323 A1 Apr. 28, 2022

Related U.S. Application Data

(60) Provisional application No. 62/793,767, filed on Jan. 17, 2019.

(51) Int. Cl.
*A61B 5/00* (2006.01)
*A61B 5/0205* (2006.01)
(Continued)

(52) U.S. Cl.
CPC .......... *A61B 5/7282* (2013.01); *A61B 5/0205* (2013.01); *A61B 5/02416* (2013.01);
(Continued)

(58) Field of Classification Search
CPC ..... A61B 5/7282; A61B 5/0205; A61B 5/026; A61B 5/1102; A61B 5/4064; A61B 5/6814; A61B 5/7264; A61B 2562/0219
See application file for complete search history.

(56) References Cited

U.S. PATENT DOCUMENTS 8,036,743 B2 10/2011 Savage et al.
2014/0371545 A1 12/2014 Ben-Ari et al.
(Continued)

FOREIGN PATENT DOCUMENTS

JP 5027797 B2 9/2012
WO 2010006370 A1 1/2010
(Continued)

OTHER PUBLICATIONS

Ahmad, Moonas, Office Action, Intellectual Property Office of the United Kingdom, Application No. GB2110342.9, Aug. 22, 2022.
(Continued)

*Primary Examiner* — Unsu Jung
*Assistant Examiner* — Laura Hodge
(74) *Attorney, Agent, or Firm* — Gavrilovich, Dodd & Lindsey LLP

(57) ABSTRACT

A headset, configured to be attached to a human head, includes an accelerometer providing a signal indicative of head acceleration due to blood flow through the brain. An analyzer evaluates a plurality of samples indicative of acceleration over time where each sample corresponds to the head movement resulting from a cardiac contraction. The analyzer identifies brain conditions at least partially based on a level of chaos of the plurality samples. The algorithm applied by the analyzer is partially formulated based on clinical data and examination of a plurality of subjects. In one example, the plurality of samples evaluated by the analyzer are indicative of the head accelerometer only in a (Continued)

single axis. In some situations, the analyzer identifies brain conditions further based on contemporaneous neurological examination of the subject.

12 Claims, 13 Drawing Sheets

(51) Int. Cl.

| | |
|---|---|
| *A61B 5/024* | (2006.01) |
| *A61B 5/026* | (2006.01) |
| *A61B 5/11* | (2006.01) |
| *A61B 5/24* | (2021.01) |
| *A61B 5/318* | (2021.01) |
| *G16H 40/67* | (2018.01) |

(52) U.S. Cl.
CPC ............ *A61B 5/026* (2013.01); *A61B 5/1102* (2013.01); *A61B 5/24* (2021.01); *A61B 5/318* (2021.01); *A61B 5/4064* (2013.01); *A61B 5/6814* (2013.01); *A61B 5/7264* (2013.01); *G16H 40/67* (2018.01); *A61B 2562/0219* (2013.01)

(56)                References Cited

U.S. PATENT DOCUMENTS

| | | | |
|---|---|---|---|
| 2015/0265161 | A1 | 9/2015 | Hernandez et al. |
| 2016/0007935 | A1* | 1/2016 | Hernandez ............ A61B 5/024 |
| | | | 600/595 |
| 2016/0081608 | A1 | 3/2016 | Lovoi et al. |
| 2016/0296153 | A1 | 10/2016 | Lovoi et al. |
| 2016/0317040 | A1* | 11/2016 | Russell .................. A61B 5/742 |
| 2018/0110667 | A1 | 4/2018 | inc |
| 2018/0296107 | A1 | 10/2018 | Harrer et al. |
| 2019/0090749 | A1* | 3/2019 | Leuthardt .............. G16H 30/40 |

FOREIGN PATENT DOCUMENTS

| | | |
|---|---|---|
| WO | 2017/004445 A1 | 1/2017 |
| WO | 2018/089035 A1 | 5/2018 |

OTHER PUBLICATIONS

Gooding, Arango, J., Extended European Search Report, European Patent Office, Application No. 20741608.2, Dec. 16, 2022.

Thomas, Shane, International Search Report & Written Opinion, PCT/US2020/013947, United States Patent & Trademark Office, Mar. 30, 2020.

Mangat, Simmi, Office Action, Canada Intellectual Property Office, Application No. 3, 126, 928, Jan. 29, 2025.

* cited by examiner

1

SYSTEMS, DEVICES, AND METHODS FOR DETECTING BRAIN CONDITIONS FROM CRANIAL MOVEMENT DUE TO BLOOD FLOW IN THE BRAIN

CROSS REFERENCE TO RELATED APPLICATIONS

This application is a U.S. National Stage Application filed under 35 U.S.C. § 371 and claims the benefit of International Application No. PCT/US2020/013947 filed Jan. 16, 2020, which application claims the benefit of priority of U.S. Provisional Patent Application Ser. No. 62/793,767, entitled SYSTEMS, DEVICES, AND METHODS FOR DETECTING BRAIN CONDITIONS FROM CRANIAL MOVEMENT DUE TO BLOOD FLOW IN THE BRAIN, filed on Jan. 17, 2019, which are incorporated by reference in their entirety herein.

FIELD

This invention generally relates to medical devices and more particularly to systems, devices and methods for detecting brain conditions from cranial movement due to blood flow in the brain.

BACKGROUND

Ballistocardiography is the measure of movement of the human body in response to the heartbeat (cardiac contraction). This process measures whole body movement. The heartbeat produces a force on the head and neck through the cerebral vasculature. The force on the brain matter produced by the heartbeat is translated to the skull. Cranial accelerometry is a method used to measure forces on the head and neck produced by the force of the heartbeat. Cranial accelerometry has been used to infer cerebral vasospasm following subarachnoid hemorrhage and to measure brain biomechanics following concussion.

SUMMARY

The disclosure provides a system comprising an accelerometer; a securing mechanism configured to secure the accelerometer to a human head having a brain such that the accelerometer is configured to generate an accelerometer signal indicative of head movement due to blood flow in the brain due to heartbeat; and an analyzer having an input configured to receive a plurality of data samples based on the accelerometer signal, each data sample indicative of the head movement associated with a different heartbeat in a single axis, the analyzer configured to determine a level of chaos of the plurality of data samples and indicate that a large vessel occlusion (LVO) has occurred in the brain when the level of chaos exceeds a threshold. In one embodiment, the accelerometer is a three-dimensional accelerometer capable of providing an axis accelerometer signal in each of three orthogonal axes. In a further embodiment, the input of the analyzer is configured to receive another plurality of data samples based on an axis accelerometer signal indicative of head movement in another axis orthogonal to the single axis, each data sample of the another plurality of data samples indicative of the head movement associated with a different heartbeat in another axis, the analyzer configured to determine a second level of chaos of the second plurality of data samples and indicate that a large vessel occlusion (LVO) has occurred in the brain when the second level of chaos exceeds a second threshold. In yet a further embodiment, the input of the analyzer is configured to receive a third plurality of data samples based on a third axis accelerometer signal indicative of head movement in a third axis orthogonal to the single axis, each data sample of the third plurality of data samples indicative of the head movement associated with a different heartbeat in the third axis, the analyzer configured to determine a third level of chaos of the third plurality of data samples and indicate that a large vessel occlusion (LVO) has occurred in the brain when the third level of chaos exceeds a third threshold. In another embodiment, the level of chaos is at least partially based on a difference between signal levels at a plurality of selected times of each of a plurality of acceleration versus time functions of the plurality of data samples. In a further embodiment, the level of chaos is at least partially based on a calculation of the plurality of acceleration versus time functions. In still a further embodiment, the calculation comprises determining a difference function for each data sample at a plurality of times, each difference function comprising a difference between the data sample and an average of all data samples. In yet a further embodiment, the calculation further comprises: rectifying and summing each difference function to generate a plurality of results; summing the plurality of results to generate a sum of results; and normalizing the sum of results to a number of data samples. In another embodiment, the calculation comprises determining a root-mean-square of the difference functions. In a further embodiment, the calculation further comprises summing the root-mean-square of the difference functions to generate a sum; and normalizing the sum to a minimum and a maximum of the average of the data samples. In another embodiment, the calculation comprises rectifying and summing each difference function to generate a plurality of results; summing the plurality of results to generate a sum of results; and normalizing the summed result to a minimum and a maximum of the average of data samples. In another embodiment, the calculation comprises applying a cross-correlation function to each data sample to an average of all data samples. In yet another embodiment, the calculation comprises determining a number of times of the plurality of times that differ from an average mean by increasing thresholds. In still another embodiment, the processor is configured to determine the level of chaos at least partially based on a shape of an acceleration versus time function of each data sample. In another embodiment, the analyzer is configured to time align the plurality of the acceleration versus time functions based on information from the plurality of the acceleration versus time functions. In yet another embodiment, the analyzer is configured to time align the plurality of the acceleration versus time plots, at least partially, from an electrocardiography (ECG) signal indicative of the cardiac contractions. In another embodiment, the analyzer is configured to time align the plurality of the acceleration versus time plots, at least partially, from an photoplethysmograph (PPG) signal indicative of the cardiac contractions. In another embodiment, the system can further comprise a transmitter configured to transmit a wireless signal indicative of the plurality of data samples; and a receiver configured to receive the wireless signal and provide the data samples to the analyzer. In a further embodiment, the system can further comprise an analog to digital converter (ADC) configured to sample the accelerometer signal to generate the plurality of data samples. In yet another embodiment, the system can further comprise a controller configured to time align the plurality of data samples before transmission of the wireless signal comprising time aligned data samples. In another embodiment, the analyzer is configured to determine the presence of the LVO condition at least partially based on neurological examination information.

The disclosure also provides a system comprising a three-dimensional accelerometer configured to generate three orthogonal signals, each orthogonal signal indicative of acceleration in an axis orthogonal to two other axes of a motion of the three-dimensional accelerometer; a securing mechanism configured to secure the three-dimensional accelerometer to a human head having a brain; and an analyzer having an input configured to receive a three sets of data samples, each data sample based on one of the orthogonal signals and indicative of the head movement associated with a different cardiac contraction in a single axis, the analyzer configured to determine a level of chaos of each set of data samples and indicate that a large vessel occlusion (LVO) has occurred in the brain when the level of chaos for at least one set of data samples exceeds a threshold.

The disclosure also provides an apparatus comprising an input configured to receive a plurality of data samples, each data sample indicative of head movement in a single axis due to blood flow through a brain initiated by a different cardiac contraction; a processor configured to determine a level of chaos of the plurality data samples that are time-aligned in reference to the cardiac contractions; and an output configured to provide an indication that a Large Vessel Occlusion (LVO) is present in the brain when the level of chaos exceeds a threshold. In one embodiment, the accelerometer signal samples are indicative of movement of the head in only a single axis. In another embodiment, the accelerometer signal samples are indicative of an output of an accelerometer secured to the head. In a further embodiment, the accelerometer is a three-dimensional accelerometer capable of providing an axis accelerometer signal in each of three orthogonal axes. In another embodiment, the level of chaos is at least partially based on a difference between signal levels at a plurality of selected times of each of a plurality of acceleration versus time plots of the plurality of accelerometer signal samples. In a further embodiment, the level of chaos is at least partially based on a calculation of the plurality of acceleration versus time functions. In yet a further embodiment, the calculation comprises determining a difference function for each data sample at a plurality of times, each difference function comprising a difference between the data sample and an average of all data samples. In still a further embodiment, the calculation further comprises rectifying and summing each difference function to generate a plurality of results; summing the plurality of results to generate a sum of results; and normalizing the sum of results to a number of data samples. In another embodiment, the calculation comprises determining a root-mean-square of the difference functions. In a further embodiment, the calculation further comprises summing the root-mean-square of the difference functions to generate a sum; and normalizing the sum to a minimum and a maximum of the average of the data samples. In another embodiment, the calculation comprises rectifying and summing each difference function to generate a plurality of results; summing the plurality of results to generate a sum of results; and normalizing the summed result to a minimum and a maximum of the average of data samples. In another embodiment, the calculation comprises applying a cross-correlation function to each data sample to an average of all data samples. In still another embodiment, the calculation comprises determining a number of times of the plurality of times that differ from an average mean by increasing thresholds. In another embodiment, the level of chaos is at least partially based on a shape of an acceleration versus time plot of each accelerometer signal sample. In yet another embodiment, a relative timing relationship between the plurality of the acceleration versus time plots is determined from the plurality of the acceleration versus time plots. In still another embodiment, the analyzer is configured to determine the presence of the LVO condition at least partially based on neurological examination information.

The disclosure provides an apparatus comprising an accelerometer configured to generate an accelerometer signal; a securing mechanism configured to secure the accelerometer to a human head having a brain; and a communication interface configured to transmit an analysis signal to an analyzer, the analysis signal based on an accelerometer signal from the accelerometer indicative of head movement due to blood flow through the brain due to cardiac contraction and based on a plurality of accelerometer signal samples, each accelerometer signal sample corresponding to a different cardiac contraction and indicative of the head movement only in a single axis. In one embodiment, the accelerometer is a three-dimensional accelerometer capable of providing an axis accelerometer signal in each of three orthogonal axes. In yet another embodiment, the apparatus can further comprise an analog to digital converter (ADC) configured to sample the accelerometer signal to generate a plurality of data samples. In another embodiment, the apparatus can further comprise a controller configured to time align the plurality of data samples before transmission of the wireless signal comprising time aligned data samples.

The disclosure also provides a method comprising receiving a plurality of data samples, each data sample indicative of head movement in a single axis due to blood flow through a brain initiated by a different cardiac contraction; determining a level of chaos of the plurality data samples that are time-aligned in reference to the cardiac contractions; and providing an indication that a Large Vessel Occlusion (LVO) is present in the brain when the level of chaos exceeds a threshold. In one embodiment, the accelerometer signal samples are indicative of movement of the head in only a single axis. In another embodiment, the accelerometer signal samples are indicative of an output of an accelerometer secured to the head. In a further embodiment, the accelerometer is a three-dimensional accelerometer capable of providing an axis accelerometer signal in each of three orthogonal axes. In another embodiment, the method includes determining the level of chaos by determining a difference between signal levels at a plurality of selected times of each of a plurality of acceleration versus time plots of the plurality of accelerometer signal samples. In a further embodiment, determining the level of chaos comprises calculating the level of chaos from a plurality of acceleration versus time functions. In yet a further embodiment, calculating the level of chaos comprises determining a difference function for each data sample at a plurality of times, each difference function comprising a difference between the data sample and an average of all data samples. In yet another embodiment, the method further comprises calculating the level of chaos further comprises rectifying and summing each difference function to generate a plurality of results; summing the plurality of results to generate a sum of results; and normalizing the sum of results to a number of data samples. In another embodiment, calculating the level of chaos further comprises determining a root-mean-square of the difference functions. In a further embodiment, calculating the level of chaos further comprises summing the root-mean-square of the difference functions to generate a sum; and normalizing the sum to a minimum and a maximum of the average of the data samples. In another embodiment, calculating the level of chaos comprises rectifying and summing each difference function to generate a plurality of results; summing the plurality of results to generate a sum of results; and normalizing the summed result to a minimum and a maximum of the average of the data samples. In another embodiment, calculating the level of chaos comprises applying a cross-correlation function to each data sample to an average of all data samples. In still another embodiment, calculating the level of chaos comprises determining a number of times of the plurality of times that differ from an average mean by increasing thresholds. In another embodiment, determining the level of chaos comprises evaluating a shape of an acceleration versus time plot of each accelerometer signal sample. In still another embodiment, the method further comprises time-aligning the plurality of data samples based on information determined from the plurality of data samples. In yet another embodiment, the method further comprises receiving neurological examination information, and determining the presence of the LVO condition based on the neurological examination information and the level of chaos.

The disclosure also provides a system comprising an accelerometer; a securing mechanism configured to secure the accelerometer to a human head having a brain such that the accelerometer is configured to generate an accelerometer signal indicative of head movement due to blood flow in the brain due to cardiac contraction; and an analyzer having a first input configured to receive a plurality of data samples based on the accelerometer signal, each data sample indicative of the head movement associated with a different cardiac contraction in a single axis, the analyzer having a second input for receiving neurological examination information from patients comprising patients that have suffered large vessel occlusion (LVO) and patients that have not suffered an LVO.

DETAILED DESCRIPTION

Figure 1:
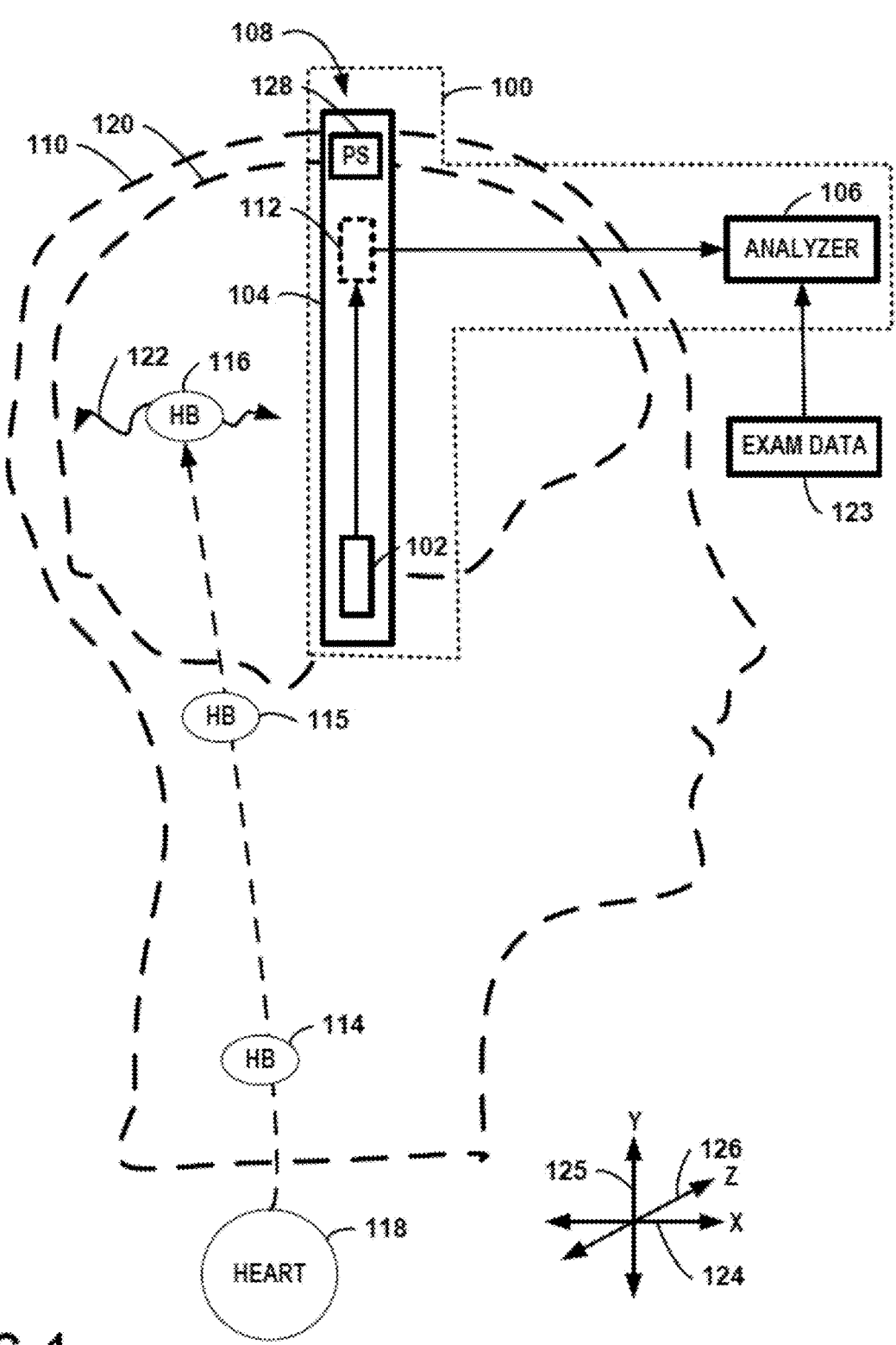
FIG. 1 is an illustration of an example of a system for observing head acceleration to evaluate brain conditions.

As used herein and in the appended claims, the singular forms "a," "an," and "the" include plural referents unless the context clearly dictates otherwise. Thus, for example, reference to "an accelerometer" includes a plurality of such accelerometers and reference to "the interface" includes reference to one or more interfaces, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The accelerometry data verses time for multiple heartbeats is called the HeadPulse recording. The heartbeat is the time of one cardiac cycle and corresponds to the R-R interval (the ECG QRS peak represents the peak of systole) from one heartbeat to the next heartbeat. The heartbeat can be used to parse the HeadPulse recording into multiple data samples where each data sample represents the accelerometer output verse time for one heartbeat.

Cranial accelerometry is a method used to measure forces on the head and neck produced by the force of the heartbeat. Cranial accelerometry has been used to infer cerebral vasospasm following subarachnoid hemorrhage (Smith et al. Neurocrit Care, 2015 December; 23 (3):364-9) and to measure brain biomechanics following concussion (Auerbach et al, Clin J Sport Med. 2015 March; 25 (2):126-3).

Acute ischemic stroke is a common and often fatal disease worldwide. Acute stroke is the leading cause of death in China, and the 5th leading cause of death in the United States. Approximately 85% of all stroke in the US is ischemic-defined as a focal reduction of blood flow to the brain by blockage of an arterial vessel. This form of stroke can be divided into Large Vessel Occlusion (LVO) and Small Vessel Occlusion (SVO) strokes. SVO stroke can best be treated with intravenous infusion of tissue plasminogen activator within the first 4.5 hours of stroke onset. LVO stroke is best treated by combination of intravenous tissue plasminogen activator followed by EndoVascular Thrombectomy (EVT). EVT involves placement of an arterial catheter into the body and introduction of a thrombectomy device through this catheter into the occluded brain artery and then withdrawal of the device along with the blood clot to open the blocked cerebral vessel.

LVO treated with EVT is now standard practice in many developed countries. EVT can only be performed at medical centers with specialized radiology equipment and with trained staff and physicians to perform the procedure. These centers are termed Comprehensive Stroke Centers (CSC) or Thrombectomy Capable Centers (TCC). This are distinguished from Primary Stroke Centers (PSC) that are hospitals that do not have this EVT capability but can treat patients with intravenous tissue plasminogen activator. Currently, in the US, there are 1110 PSC and only 191 CSC/TCCs; this means that only 17% of acute stroke centers in the US can handle LVO patients. When a PSC encounters an LVO patient, the patient requires transfer to a CSC/TCC and the time taken in this transfer worsens the brain injury to the patient.

The time from stroke symptom onset (when the blood clot closed the large vessel) to successful thrombectomy directly predicts the clinical outcome for the stroke patient. The longer it takes to begin performing the procedure the worse the patient does and the sooner the procedure is performed the more likely the patient will be cured.

The time to successful EVT depends mostly on the time it takes to transport the patient from where they are discovered to a CSC/TCC. Once a patient arrives at a CSC/TCC, EVT is performed often within minutes of arrival to reduce morbidity. However, transport times to the CSC/TCC are highly variable based on the prehospital triage process within the geographic region.

The heuristic of having prehospital providers transport all patients with a suspected stroke to CSC/TCCs overwhelms these few centers, while transporting suspected stroke patients to the closest stroke ready hospital (typically a PSC) risks delaying the time to EVT because a secondary transport from the PSC to CSC/TCC is required.

A system of transporting LVO patients to CSC/TCC and non-LVO patients to PSCs is a strategy to maximize efficiency and improve outcomes from stroke. However, determining if a patient has an LVO stroke in the prehospital setting is problematic.

The standard of care to determine LVO is to perform a brain imaging study that images the patency of intracranial vessels. This is most commonly a computed tomography angiogram (CTA) and requires a CT scanner. Some communities in the US are placing CT scanners in ambulances but this is an impractical solution because of cost and lack of availability of physicians to interpret imaging and interact with paramedics.

Performance of a neurological examination and interpreting the signs and symptoms is approximately 80% accurate in determining LVO if done by a neurologist or other medical professional with training in stroke. Prehospital medical professionals do not achieve this accuracy. Therefore, even if a neurologist was present during the clinical encounter (via telemedicine link or physical presence) around 20% of patients would be wrongly triaged.

Outside of using a portable CT scanner, a biometric that measures some change in the human brain during LVO could be combined with components of the neurological exam to arrive at a higher accuracy in LVO detection.

The forces produced by the heart are transmitted to the human skull along large arterial branches including the carotid and vertebral arteries. Minute head movements produced by transmission of these forces is termed the Head-Pulse. The HeadPulse recording is a single or set of time-domain waveforms that can be transduced with a position, velocity, force or impulse-sensitive apparatus, including accelerometers, impulse detectors, velocity sensors and strain gauges. These sensors are placed on the patient's head where they can transduce the HeadPulse. The transducers produce an electrical signal that can be recorded in analog format or converted to digital form and then displayed on an oscilloscope or digital monitor. The HeadPulse recording can be obtained in healthy subjects to define a reference standard. The HeadPulse can be obtained in patients with various conditions and compared to the HeadPulse characteristics of normal patient to determine a particular waveform signature of the disease process. Although the examples discussed below are directed to detecting LVO, the techniques discussed herein may be applied to other disease processes including, for example, acute ischemic stroke, intracerebral hemorrhage, concussion, traumatic brain injury, brain edema and prognosis following cardiac arrest. The techniques may also be applied to evaluating clinical conditions during anesthesia and sleep. Particular neurodegenerative conditions including Alzheimer's Disease, fronto-temproal dementia, Parkinson's disease, synucleinopathies, progressive supra-nuclear palsy, prion disease, multisystem atrophy, and other neurodegenerative diseases that cause brain atrophy and protein deposits within the atrophic brain can be diagnosed by variation of the Head-Pulse techniques from known standards.

Measurement of the HeadPulse and analysis of the waveform data obtained in combination with some components of the neurological exam is a method to improve the accuracy of LVO stroke diagnosis and therefore can be the basis for triage decisions to move a stroke patient to a center that provides EVT.

The HeadPulse can be obtained and analyzed by building a headset that houses impulse, acceleration, velocity and/or position sensors that make contact to the human head, while recording the time of contemporaneous heartbeats. The HeadPulse recordings are then submitted to a computer algorithm that incorporates these signals along with contemporaneous clinical data (e.g., level of consciousness, limb strength, etc.) to provide an immediate, probabilistic prediction of the presence or absence of a disease (e.g., acute LVO stroke) or clinical state (e.g. sleep or anesthesia) and make that information available to a trained user of the device for clinical decision making.

For the examples discussed herein, a headset, configured to be attached to a human head, includes at least one 3-axis accelerometer providing a signal indicative of head motion due to blood flow through the brain. An analyzer evaluates a plurality of samples indicative of acceleration over time where each sample corresponds to head acceleration resulting from a heartbeat. The analyzer identifies brain conditions using an algorithm that is based at least partially on head acceleration at least partially based on a level of chaos of the plurality of samples. The algorithm applied by the analyzer is partially formulated based on clinical data where the clinical data is categorized based on a cohort of subjects with and without an LVO. In one example, the plurality of samples evaluated by the analyzer are indicative of the head movement only in a single axis. In some situations, the analyzer identifies brain conditions further based on contemporaneous neurological examination of the subject.

FIG. 1 is an illustration of an example of a system 100 for observing head acceleration to evaluate brain conditions. For the examples discussed herein, the system 100 determines, or at least evaluates a probability of, whether a Large Vessel Occlusion (LVO) has occurred in a subject's brain. The devices and techniques described herein can be applied to other diagnostic and prognostic situations although the examples below are directed to determining whether an LVO condition has resulted in a stroke in a subject. Generally, an analyzer evaluates a plurality of data samples indicative of head acceleration due to a plurality of heart beats to determine a level of chaos of the data samples. For the examples below, the data samples are digital representations of an output signal of an accelerometer showing acceleration as a function of time for each heartbeat. Based on an evaluation of the digital representations that are time aligned relative to the heartbeat, a level of chaos is determined. As discussed herein, chaos is a subjective term used to describe the lack of repetitive correlated accelerometry data samples. Chaos can be numerically defined by several measures that in large part are based on the degree of dissimilarity between any single measurement following a heartbeat and some estimate of the mean of all measurements from a HeadPulse recording.

For the example of FIG. 1, the system 100 includes an accelerometer 102, a securing mechanism 104 and an analyzer 106. In some situations, the analyzer 106 is part of a headset 108 that is secured to the subject's head 110. As discussed below, in one example, the analyzer 106 may be separate from the headset 108 and a communication interface 112 can transmit information to the analyzer 106. In other examples, data is stored in memory in the headset 108 and is transferred to the analyzer 106 over a wired or wireless connection. In other situations, the data is stored on a removable memory (e.g., memory card, flash card, memory cartridge, memory stick, etc.) at the headset 108 and moved to the analyzer 106 to transfer the data. In situations where the analyzer is implemented with a processor within the headset, a separate memory device may be omitted. Therefore, the data may be analyzed by a processor within the headset without a memory device in the headset, by a processor within the headset with a memory device in the headset, stored by a memory device in the headset and mechanically removed to be analyzed by a processor that is external to the headset, or stored by a memory device in the headset and transmitted wirelessly to a processor that is external to the headset.

The communication interface 112 is illustrated with dashed lines to indicate that the communication interface 112 can be omitted in some situations such as when the analyzer 106 is part of the headset 108. The various functions and operations of the blocks described with reference to the system 100 may be implemented in any number of devices, circuits, or elements. Two or more of the functional blocks described shown in the figures may be integrated in a single device, and the functions described as performed in any single device may be implemented by several devices or elements.

As is known, a heartbeat produces a force on the head and neck through the cerebral vasculature. The force on the brain matter produced by a heartbeat is translated to the skull. Therefore, the head 110 of a subject moves in response to each heartbeat 114, 115, 116 of the heart 118 as blood is pumped through the brain 120. For the examples herein, the accelerations 122 are detected with the accelerometer 102 and evaluated to determine if a Large Vessel Occlusion (LVO) has occurred in the subject. For one technique, several signal samples are collected where each signal sample corresponds to a heartbeat 114, 115, 116 and the signal samples are evaluated by the analyzer 106 to determine a level of chaos of the collection of signal samples. Although, generally, the probability that a stroke due to LVO has occurred increases with a higher level of chaos, a refined algorithm based on clinical data and head movement data for multiple test subjects can be developed to increase accuracy of LVO identification. As described in further detail below, any of numerous evaluations, calculations, or signal processing techniques can be used to determine the level of chaos. The chaos level can be represented by a numerical value that is compared to a threshold where a value above the threshold is determined to be an indication that an LVO stroke has occurred. For the examples herein, the algorithm applied to the data is partially based on neurological examination and clinical data from a large number of subjects to refine the algorithm. For the example of FIG. 1, the analyzer 106 also evaluates contemporaneous examination and clinical data 123 to determine the presence or absence of an LVO condition. Therefore, for at least some situations, a person performs an examination of the subject and enters the results into the analyzer 106. Accordingly, the analyzer includes, or is connected to, an input device, such as keyboard, mouse, touchpad, microphone, or touchscreen, for example. The analyzer may also include, or be connected to, output devices such a visual display and speaker.

The accelerometer 102 detects acceleration in at least one direction (axis) and generates an accelerometer signal based on the acceleration of the head. In one example, the accelerometer is a 3-axis accelerometer, sometimes referred to as a 3-dimensional (3D) accelerometer, that generates three signals. Each signal corresponds to acceleration in one of the three axes (X, Y, and Z) 124, 125, 126. Each axis is orthogonal to the other two axes. The three signals generated by the accelerometer, therefore, are also orthogonal.

In some situations, signal samples from only a single axis are collected and analyzed. In other situations, the chaos of signal samples in one axis is determined and the chaos of signal samples in another axis are evaluated where the two chaos values can then be evaluated to determine the likelihood of an LVO condition. For example, signal samples for each of three axes can be evaluated independently to determine chaos in each axis where the resulting values are further processed to determine the probability of an LVO condition. In other situations, the two or more chaos values can be averaged and then compared to a threshold. Therefore, data from multiple axes can be evaluated using different techniques.

In some situations, the headset 108 may include more than one accelerometer. The data from each accelerometer can be evaluated independently to determine chaos in each axis of each accelerometer where the resulting values are further processed to determine the probability of an LVO condition. In other situations, the data from multiple axes from each accelerometer are processed and the resulting evaluation data is further processed with evaluations of data from other accelerometers. Therefore, data from any number of axes and accelerometers can be processed and evaluated in numerous ways.

A power supply 128 provides electrical power to the components of the headset 108. For the examples herein, the power supply 128 is a battery within the headset 108 where the battery may include one or more cells. The battery may be disposable or rechargeable. Where the battery is rechargeable, the headset may include electrical circuitry and/or a charging interface to facilitate charging of the battery. In some situations, the power supply may be external to the headset. For example, an AC to DC power supply or an external battery pack may be connected to the headset. Also, the charging interface may be an interface that facilitates wireless charging.

Figure 2A:
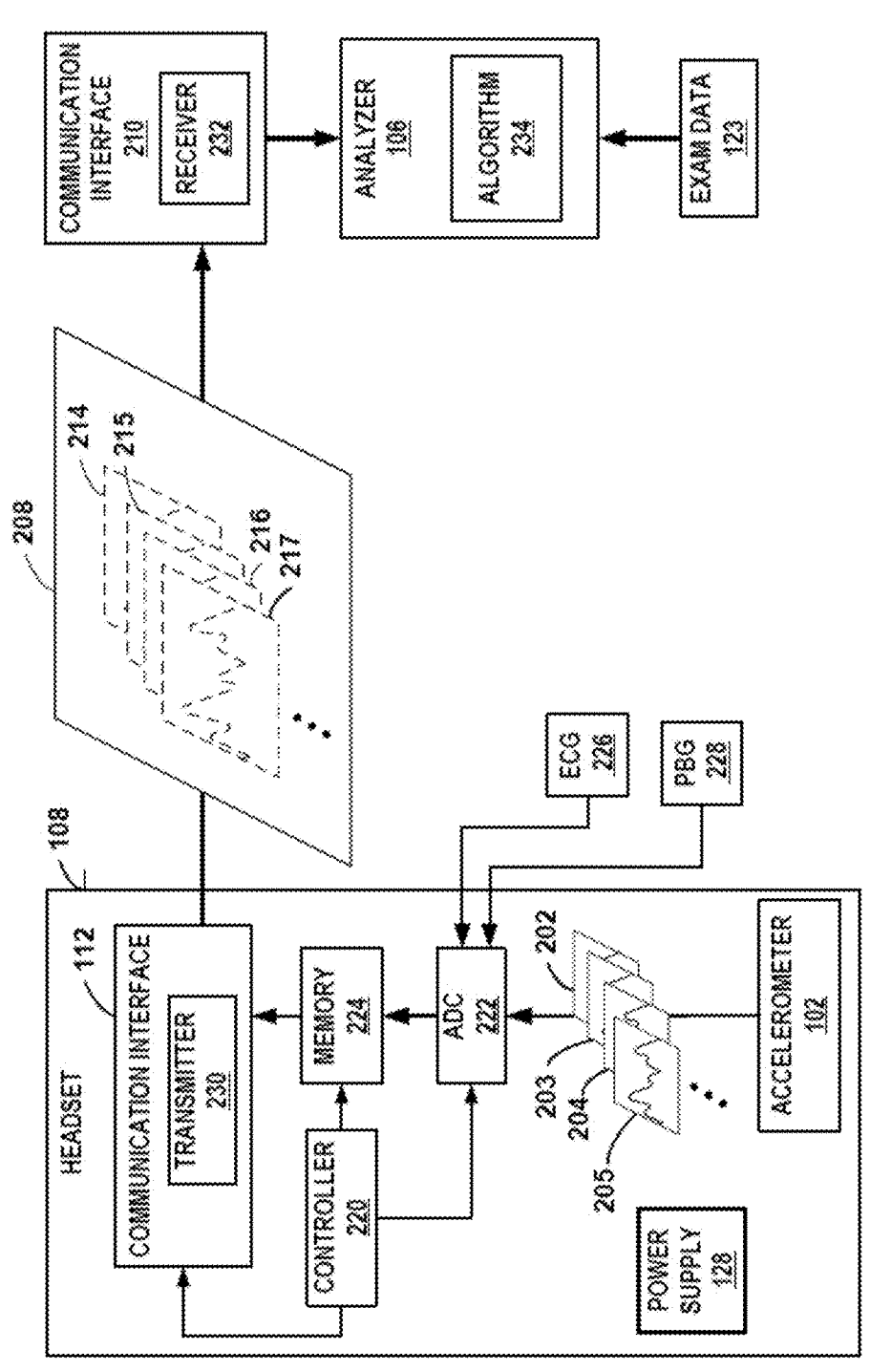
FIG. 2A is a block diagram for an example where the headset includes a communication interface.

FIG. 2A is a block diagram of an example where the headset 108 includes a communication interface 112. During operation, the headset 108 is placed on the subject's head 110 with the securing mechanism 104. The accelerometer 102 detects acceleration of the head in at least one direction (axis) for several heartbeats to generate multiple signal samples 202-205 where each signal sample is associated with a heartbeat. The communication interface 112 transmits data 208 corresponding to the signal samples 202-205 to the analyzer 106. For the example, the data 208 is a digital representation of the signal samples 202-205 and is received by a communication interface 210 connected to or part of the analyzer 106.

The data 208 in the examples, therefore, includes data samples 214-217 indicative of the acceleration measured by the accelerometer as a function of time. The data samples may be a plot, graph, table, listing of associated values, data string, or other representation of the acceleration versus time function of the accelerometer output. The data samples 214-217 may include other data that is related to acceleration and time function in some circumstances. For example, the data 208 may reveal position as a function of time or velocity as a function of time. For the examples discussed below, the data samples are acceleration versus time representations that can be processed to determine the level of chaos over several samples. For an example discussed below, the head movement is transduced by a 3-axis accelerometer and the analog signals from each axis is digitized for processing by the analyzer. A time sequence of such digitized data can be referred to as a HeadPulse recording.

The data representing the acceleration (or other data indicative of movement) of the head can be conveyed in any of several ways depending on the particular implementation. In the example of FIG. 2, the analog output of the accelerometer is converted to digital data that is periodically transmitted to the analyzer and is indicative of acceleration over time for several heartbeats. For the example, a controller 220 instructs a parallel analog to digital converter (ADC) 222 to convert the periodic analog HeadPulse recording generated by the accelerometer 102. The digital data is stored in a memory unit 224. An example of a suitable ADC and memory unit includes a 24-bit ADC converting the analog signals simultaneously to digital format and storing the data in a MicroSD memory through a Serial Peripheral Interface (SPI). For the example, signals from an Electrocardiography (ECG) 226 and light emitting diode (LED) sensor 228 producing a photoplethysmograph (PPG) are used to set a time reference for the acceleration signals. As is known, PPG is a waveform that resembles the arterial pulse. The ECG signals and/or PPG signals can be omitted. In some situations, for example, the timing of the samples can be derived from differences in accelerometry waveforms or data samples obtained by opposite head positions. This is a measurement of scalp plethysmography. Other techniques may be used to obtain heartbeat timing information. For example, a sensor can be placed on an artery such as an accelerometer on the carotid artery. Therefore, the heartbeat timing may be obtained or derived from an ECG signal, a PPG signal, the HeadPulse recording, a sensor on an artery or any combination thereof.

The controller 220 is any controller, processor, electrical circuit, logic circuit, processing circuit, or processor arrangement that manages the functions described herein as well as facilitating the overall functionality of the headset. An example of a suitable controller 220 is a microprocessor and supporting circuitry operating in accordance with an nRF 52 Cortex M-4 processor architecture.

The data 208 is retrieved from the memory 224 and transmitted to the analyzer 106. The communication interface 112 in the headset 108 includes at least a transmitter 230 and the communication interface 210 connected to the analyzer 106 includes at least a receiver 232. Although signals between the two communication interfaces can be conveyed over wires or cables, a wireless interface is used in the example. The communication interfaces 112, 210 in the example operate in accordance with Bluetooth communication standards. Examples of other suitable wireless communication include techniques in accordance with Wi-Fi and ZigBee communication standards. In some situations, the communication interfaces 112, 210 may operate in accordance with a proprietary wireless interface or protocol. In still other situations, an optical interface can be used.

Therefore, the transmitter 230 in the communication interface 112 transmits the digital data 208 representing the captured samples 202-205 to a receiver 212 in communication interface 210 connected to the analyzer 106. In some situations, the data can be stored in memory at the headset and transferred to the analyzer when connected to the analyzer 106 through a wired connection, or transmitted over a wireless interface. In other examples, the analog output of the accelerometer is converted to digital data that transmitted to the analyzer in real time. Accordingly, for at least some examples, the digital data 208 is transmitted wirelessly to the analyzer 106 where the digital data 208 represents a level of acceleration as a function of time over several heartbeats. The resulting data samples 214-217 of acceleration versus time for each heartbeat corresponding to the analog samples 202-205 are collectively evaluated by the analyzer 106. In the interest of brevity and clarity, FIG. 2 shows four data samples 214-217 representing the four analog signal samples 202-205. Any number of signal samples and/or data samples, however, may be captured and evaluated. The collection of data samples can be referred to as a HeadPulse recording.

The analyzer 106 is any computer, processor, server or other device that runs code to apply an algorithm 234 to the data samples 214-217 to produce an indication of whether an LVO condition is present in the subject. In one example, the analyzer 106 is a local desktop or laptop computer running a program. In other situations, the analyzer 106 is an application running on a server. The analyzer 106, therefore, may be implemented in the "cloud" where the data 208 is provided through a network such as the Internet, Intranet, or other private communication network. In still other examples, the analyzer may include an application running on a smart phone or tablet. In still other examples, the algorithm can be incorporated into the microprocessor 220 producing output through a series of lights on the headset. The algorithm 234 may be based on several comparisons, evaluations, and mathematical calculations and may be adjusted, revised, refined, or otherwise based on examinations and clinical data 123. For the examples discussed herein, the algorithm 234 that is applied by the analyzer 106 in the system 100 is refined and partially based on neurological examinations and clinical data 123. During the algorithm refinement procedure for the example, system 100 includes the same components that would be used in the field and is used to obtain data from several subjects. The analyzer 106 applies the algorithm 234 and determines a binary or graded result indicating the presence or absence of an LVO condition in the subject. Refinement of the algorithm 234 is based on comparing the algorithm's prediction of LVO and the actual presence or absence of LVO determined by angiography. For example, if the result indicates the absence of an LVO condition and a reference result, such as a Computed Tomography Angiography (CTA), indicates the presence of an LVO condition, the algorithm is adjusted such that the result will indicate the presence of an LVO condition for that same set of data. Examples of neurological examinations and clinical data 123 suitable for adjusting the algorithm include various component of the National Institutes of Health Stroke Scale (NIHSS), measuring arm strength asymmetry (value of 0 if both arms move equally, or do not move at all, and 1 if the arms move asymmetrically based on instruction to the patient or via mimicry), or other standard neurological examination elements customary to the field of neurology.

In some situations, the results, data, and LVO status can be subjected to machine learning, such as MATLAB, Classification Learner, using a classification tree. The results of the classification can be used to refine the algorithm. In some situations, input to the classification algorithm is in the form of a spreadsheet that incorporates clinical examination results and chaos measurements. For the clinical exam, for example, a variable for asymmetric limb weakness with value of 0 or 1 is entered for the patient encounter, or numerical elements of the NIHSS score. Various derivations of chaos are entered as row data on the same spreadsheet data row. Finally, the determination of LVO by angiography is entered as the outcome variable for the classification algorithm. The data from multiple patients with and without LVO are submitted to the classification algorithm with care to prevent over fitting. The output is a model that can then be tested prospectively on patient data not used in the generation of the algorithm to tests the performance characteristics of algorithm. For the examples, successive bootstrapping of data refines the algorithm.

Figure 2B:
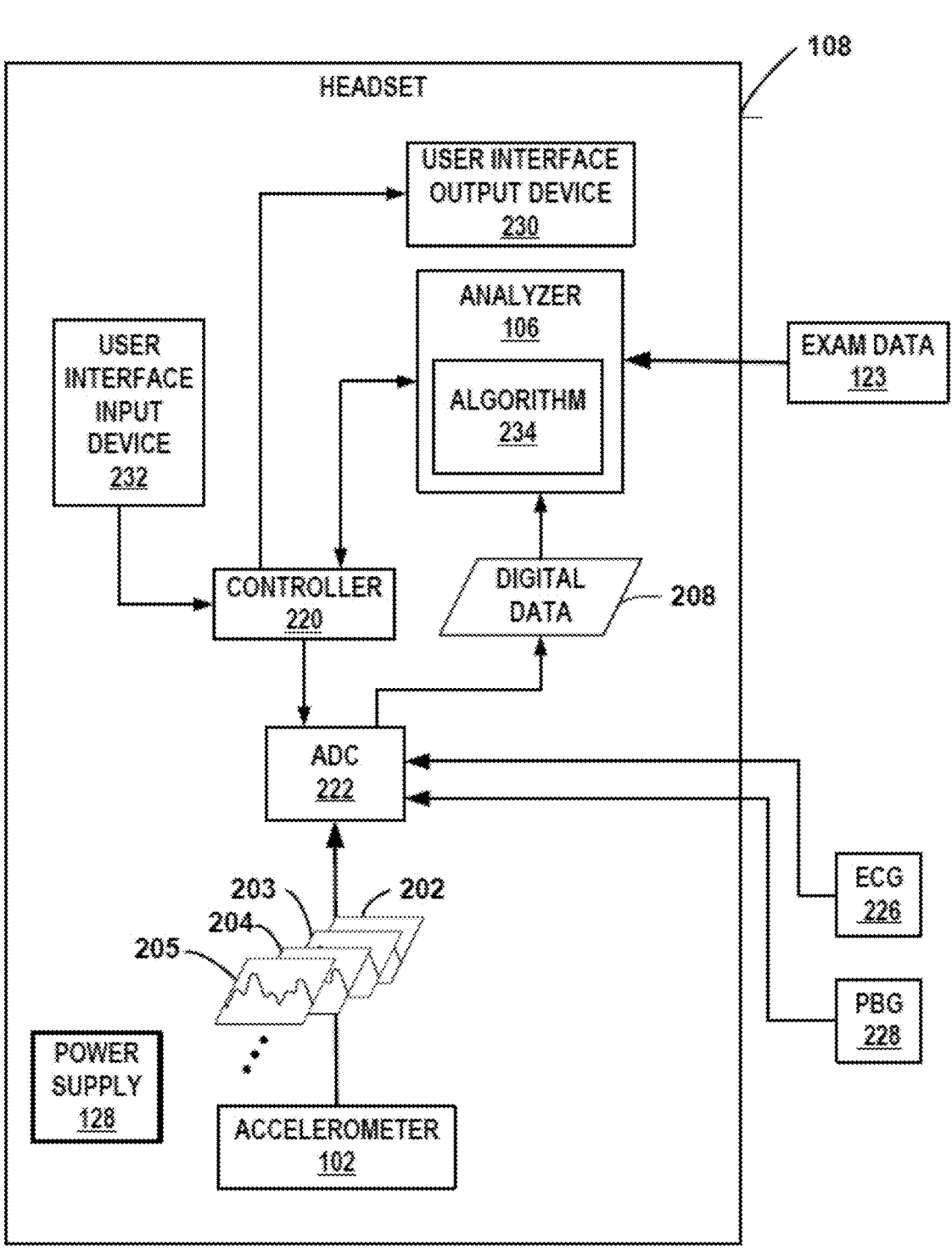
FIG. 2B is a block diagram for an example where the headset includes an analyzer and a user interface.

FIG. 2B is a block diagram of an example of headset 108 where the system 100 is implemented within the headset 108. For the example, the headset includes a user interface output device 230 and a user interface input device 232 as well as other components discussed with reference to FIG. 2A. The user interface output device 230 is any interface that provides information to the user and may include a visual output device and/or an audio output device. Examples of visual output devices include visual displays, lights, and LEDs. Where lights or LEDs are used, one or more LEDs or lights may be used where the duration, color, frequency/duty cycle of activation and/or intensity conveys information to the user. Where more than one LED or light is used, information can be conveyed to the user based on the selection of the particular active lights or LEDs in addition to the duration, color, frequency/duty cycle and intensity. Multicolor LEDs can be used in some situations. Examples of suitable audio output devices include speakers and buzzers where the tones, duration, frequency/duty cycle of activation and/or intensity of the sound produced provides information to the user. In some situations, the audio output device may generate voice or music to convey information. The controller provides the appropriate signals to the user interface output device 230 to produce the visual and/or audio outputs that provide the information to the user. The user interface input device 232 is any device that allows the user to provide information to the system. The user interface input device 232 provides signals or values to the controller 220 that are indicative of the information entered by the user. In some situations, the user interface input device 232 may include one or more switches or buttons. Other examples include keypads, touchpads, and touchscreen displays. In some situations, the user interface input device 232 may include a microphone that provides signals to the controller that correspond to voice commands provided by the user and that can be interpreted by the controller 220. The user interface input device 232 may include a combination of different types of input devices in some situations.

The system in the example of FIG. 2B is similar to the system in the example of FIG. 2A except that for the system of FIG. 2B, some components are omitted, the analyzer is implemented within the headset 108, and a user interface 230, 232 is included. A communication interface is not required to convey the data to the analyzer and is therefore omitted. The analyzer may be implemented using a processor, controller, processor arrangement, or other electrical circuitry. Although in the example of FIG. 2B the controller 220 is shown as separate from the analyzer 234, both devices as well as other functionality may be implemented on a single processor. The data capture and analysis operation of the example of FIG. 2B is similar to the operation discussed with reference to FIG. 2B except that the digital data is 208 representing the acceleration signals generated by the accelerometer are provided directly to the analyzer without transmission to a separate device.

Figure 3:
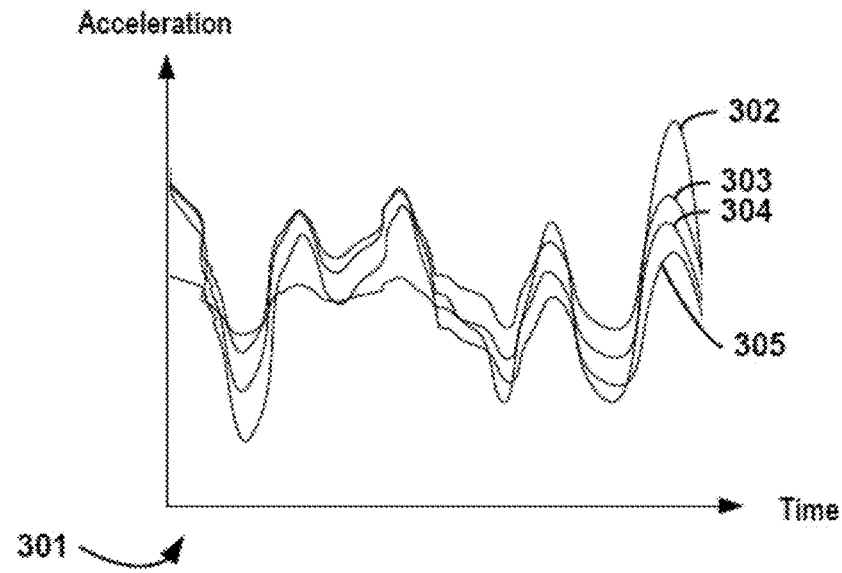
FIG. 3 is an illustration of graphical representations of two sets of acceleration signals over time from a single axis of a single accelerometer.
Figure 3:
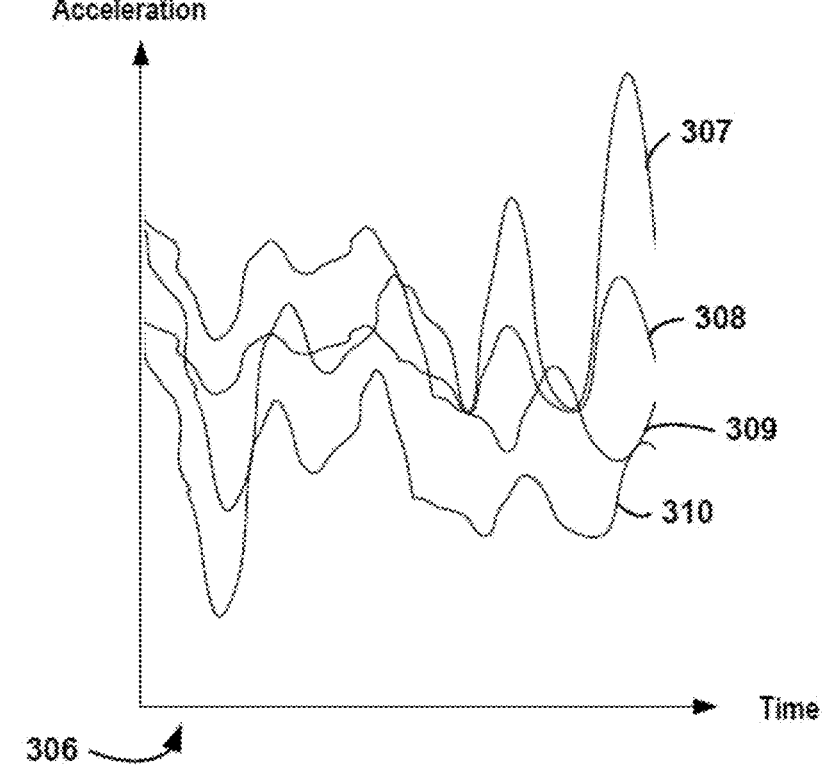

FIG. 3 is an illustration of graphical representations of two sets of acceleration over time data samples from a single axis of a single accelerometer. The two graphical representations each include four data samples of acceleration as a function of time. The data samples in FIG. 3 are not necessarily derived from captured data and are intended to provide a visual interpretation of the chaos between data sample sets of HeadPulse recordings. In the interest of clarity and brevity, only four data samples are shown in each graphical representation set. As mentioned above, numerous data samples are typically captured and evaluated. In the first graphical representation 301, the four data samples 302-305 represent possible acceleration plots captured by the headset for a subject that does not have an LVO condition. In the second graphical representation 306, the four data samples 307-310 represent possible acceleration plots captured by the headset for a subject that has an LVO condition. Generally, the data samples 302-305 have less variations between the data samples than the data samples 307-310. The chaos of a set of data samples is related to differences between data samples where the differences may be in one or more of amplitude, phase, and slope of the waveforms. The illustrations of FIG. 3 provide a visual representation of the difference in chaos between two sets of data samples. The chaos may be quantified using one more mathematical functions or processes applied by the algorithm.

Figure 4:
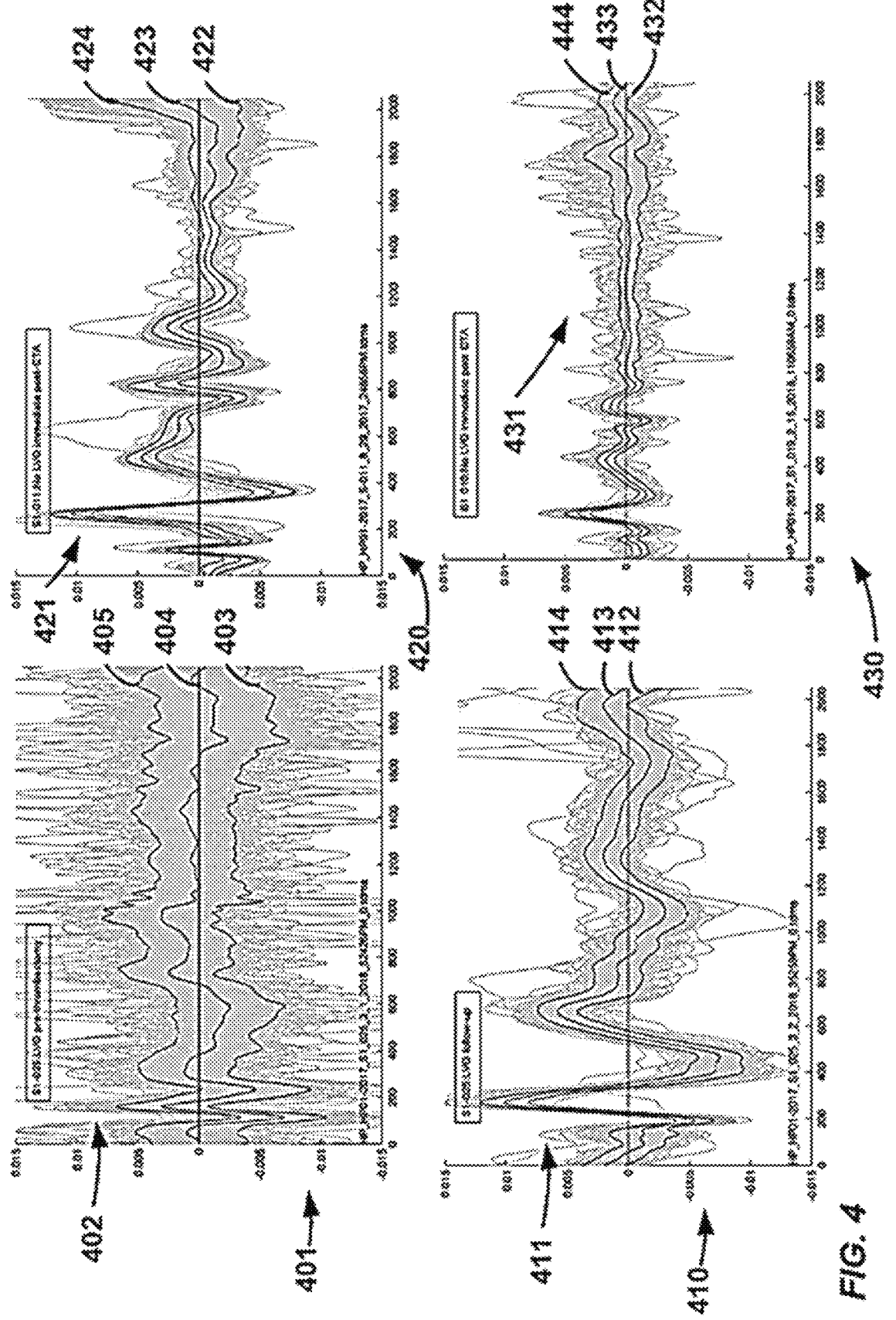
FIG. 4 is an illustration of an example of chaos of cranial accelerometry during a plurality of cardiac cycles for three different conditions.

FIG. 4 is an illustration of an example of chaos of cranial accelerometry during a plurality of heartbeats for three different conditions. A first graphical relationship 401 includes a plurality of traces 402 of acceleration as a function of time for a subject with an LVO stroke. The X axis is time and the Y axis is acceleration in gs. The waveforms of the plurality of traces are time aligned with an ECG trigger at time zero. The mean of the plurality of signals is shown as line 404, the upper one standard deviation of bin-wise values is shown as line 405 and the lower one standard deviation is shown as line 403. A second graphical relationship 410 includes a plurality of traces 411 of acceleration as a function of time for the subject of the first graph following thrombectomy. The first graphical relationship 401 shows little correlation between a data trace morphology and the ECG. After the thrombectomy, however, the second graph 410 shows a higher correlation with the ECG. A third graphical relationship 420 includes a plurality of data samples 421 of acceleration as a function of time for a subject with an acute small vessel stroke. A fourth graphical relationship 430 includes a plurality of data samples 431 of acceleration as a function of time for a subject with a stroke mimic that was actually a migraine. Visual inspection of the data samples in 401 and 410 show resolution of chaos following thrombectomy. The presence of chaos in 401 is indicative that the subject is experiencing an LVO stroke. This forms the basis for biometric prediction of LVO occlusion. The patient represented in 421 is having a stroke at the time, but not due to LVO. The lack of chaos in the data samples is indicative that this patient does not need to be treated with thrombectomy. The patient in 430 is suffering from migraine that simulates stroke. This patient does not need to be treated for LVO. Contrasting data samples in 401, 420 and 430, a trained eye can discern that the patient in 401 is different from patients in 420 and 430. This is irrespective of having a pre-stroke baseline measurement on each subject to arrive at this conclusion.

Figure 5:
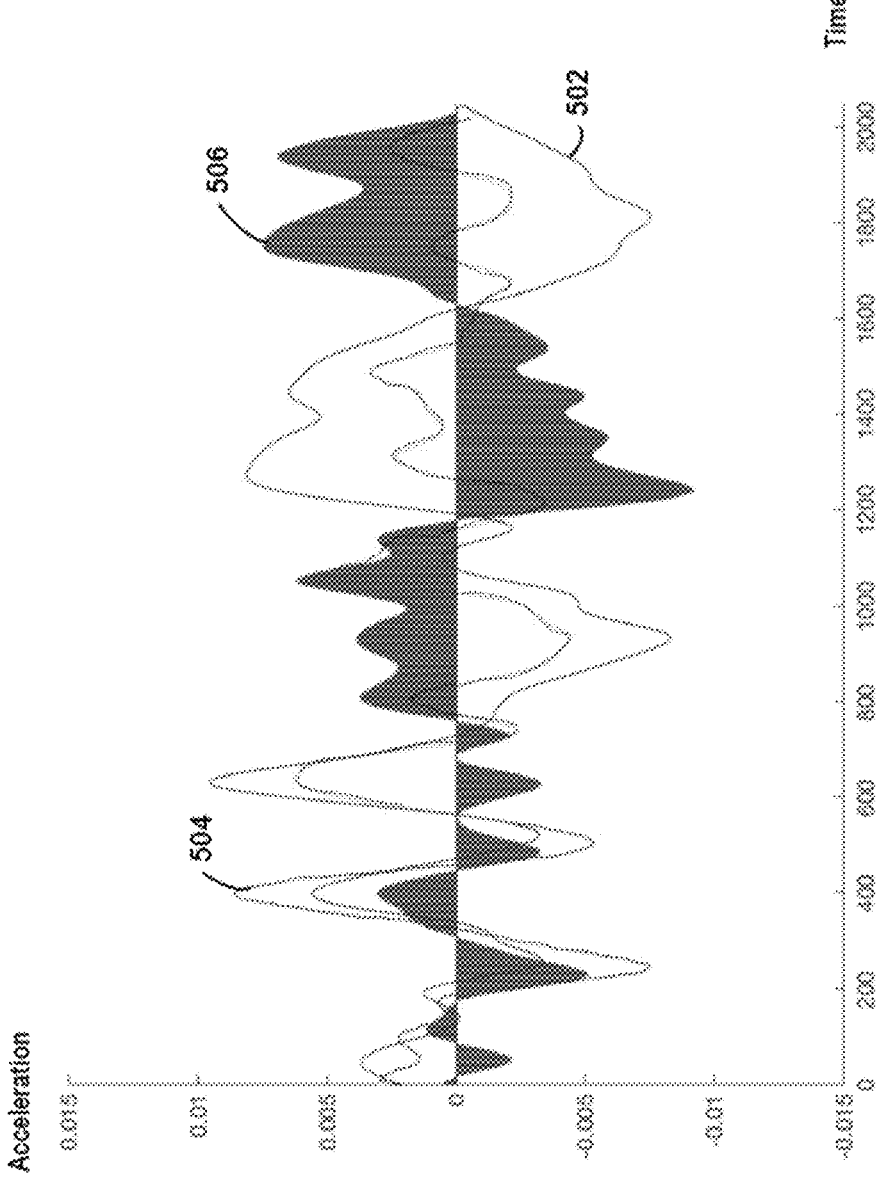
FIG. 5 is an illustration of an example of a method to measure chaos of cranial accelerometry during a heartbeat.

FIG. 5 is an illustration of an example of how one measure of chaos is derived from a plurality of data samples. The abscissa is proportionate to time and contains 2048 bins where the data samples are scaled to a 2048 bin range based on the average heart rate. The ordinate is acceleration in the vertical axis measured in gs. An ECG trigger is used to set a reference time at time zero (0). A single data sample 502 of the vertical acceleration is shown as a solid line. The signal-averaged data samples 504 for all data samples is shown as a dotted line. The difference 506 between the single data sample and the signal-averaged data samples for each bin is shown as a shaded solid line.

The chaos of a set of data samples can be determined using different techniques. Some examples of chaos calculation are discussed below. For the examples, a HeadPulse recording is parsed into N data samples based on the heartbeat and are then further processed using one or more of the following calculations.

In a first chaos calculation, the RMS difference between each pair of data samples is calculated data point by data point, the results, squared, the mean taken and the square root calculated.

In a second chaos calculation, the mean and one standard deviation less than the mean and one standard deviation greater than the mean are calculated for all the data samples from a HeadPulse recording. For each data sample the number of data points that fall outside one standard deviation are tallied. The number of data samples is plotted on the y-axis and the number of data points that are outside one standard deviation is plotted on the x-axis. Ratios of values from the resulting graph are used as numerical value of chaos.

In a third chaos calculation, the RMS differences are calculated by quartile between the mean of all data samples in a HeadPulse and each data sample. A histogram is calculated for each quartile and the histogram curve is fit with a normal distribution. Sigma, the width of the normal fit is used for each quartile and ratios between quartile sigmas are used as numerical values of chaos.

In a fourth chaos calculation, the mean of all the data samples from a HeadPulse recording is calculated and an absolute value is taken. An integral of the result is made over all the data points. Ratios of quartile values are used as numerical values of chaos.

In a fifth chaos calculation, the RMS difference between each data sample and the mean of all data samples from a HeadPulse recording is calculated data point by data point, the results, squared, the mean taken and the square root calculated.

In a sixth chaos calculation, the number of bins in the 2048 trace that differ from the mean are counted by increasing thresholds.

Figure 6:
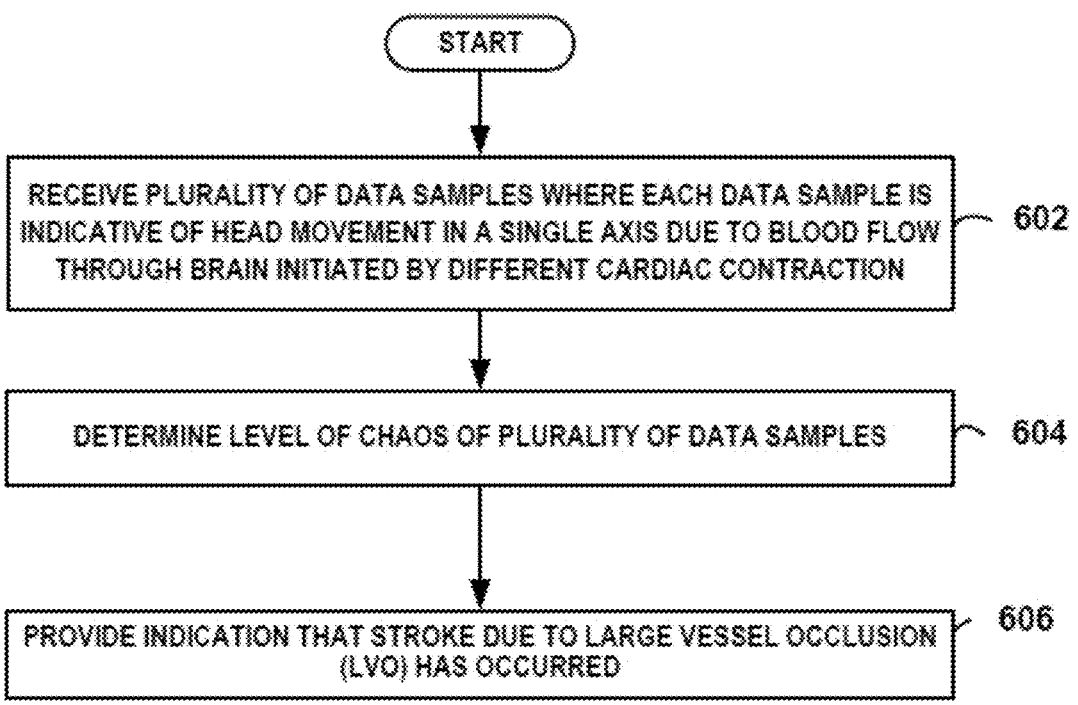
FIG. 6 is a flow chart for an example of a method for identifying brain conditions.

FIG. 6 is a flow chart for an example of a method for identifying brain conditions. The method may be performed by any combination of hardware and code. Examples of some suitable techniques include running code on a computer, tablet or smartphone to perform the steps discussed below. Additional steps to those described with reference to FIG. 6 may be performed in many situations.

At step 602, a plurality of data samples is received where each data sample is indicative of head acceleration in a single axis due to blood flow through the brain. For the example, each data sample is a digital representation of acceleration as a function of time. As described above, a suitable technique for capturing the data samples includes attaching a three-axis accelerometer to the head of the subject where the analog accelerometer signals are converted to the digital data samples. The data samples are time-aligned in reference to the heartbeat either based on information from the data samples or from some other signal related to the heartbeat. Examples of such signals include ECG and PPG signals as discussed above.

At step 604, a level of chaos of the data samples is determined. Chaos can be numerically defined by several measures that in large part are based on the degree of dissimilarity between any single data sample following a heartbeat and some estimate of the mean of all measurements following a plurality of heartbeats or between a data sample and all other data samples. The numerical value may be determined or calculated using a variety of techniques. Calculations such a root-mean-square calculations can be applied to the difference functions and results can be normalized to produce a numerical chaos value.

At step 606, an indication that a stroke due to LVO has occurred is provided to a user. For the example, the indicator that a stroke has occurred is provided if the level of chaos exceeds a threshold where particular clinical examination conditions exist. For the examples herein, information pertaining to the contemporaneous clinical neurological exam findings, such as limb strength or components of the NIHSS score, are integrated with the biometric data from 604. The classification algorithm derived from data from multiple patients with LVO, and patients without, is then used to predict either a binary or a granular probability of LVO in the patient being examined. The algorithm, therefore, can determine the existence of LVO based on the chaos level and neurological and clinical data obtained at the time the acceleration data is obtained on the subject. Examples of indications include, text or symbols provided though a visual display, or LED lights of various colors, although any indicator can be used to convey wherein the LVO condition is present.

Figure 7:
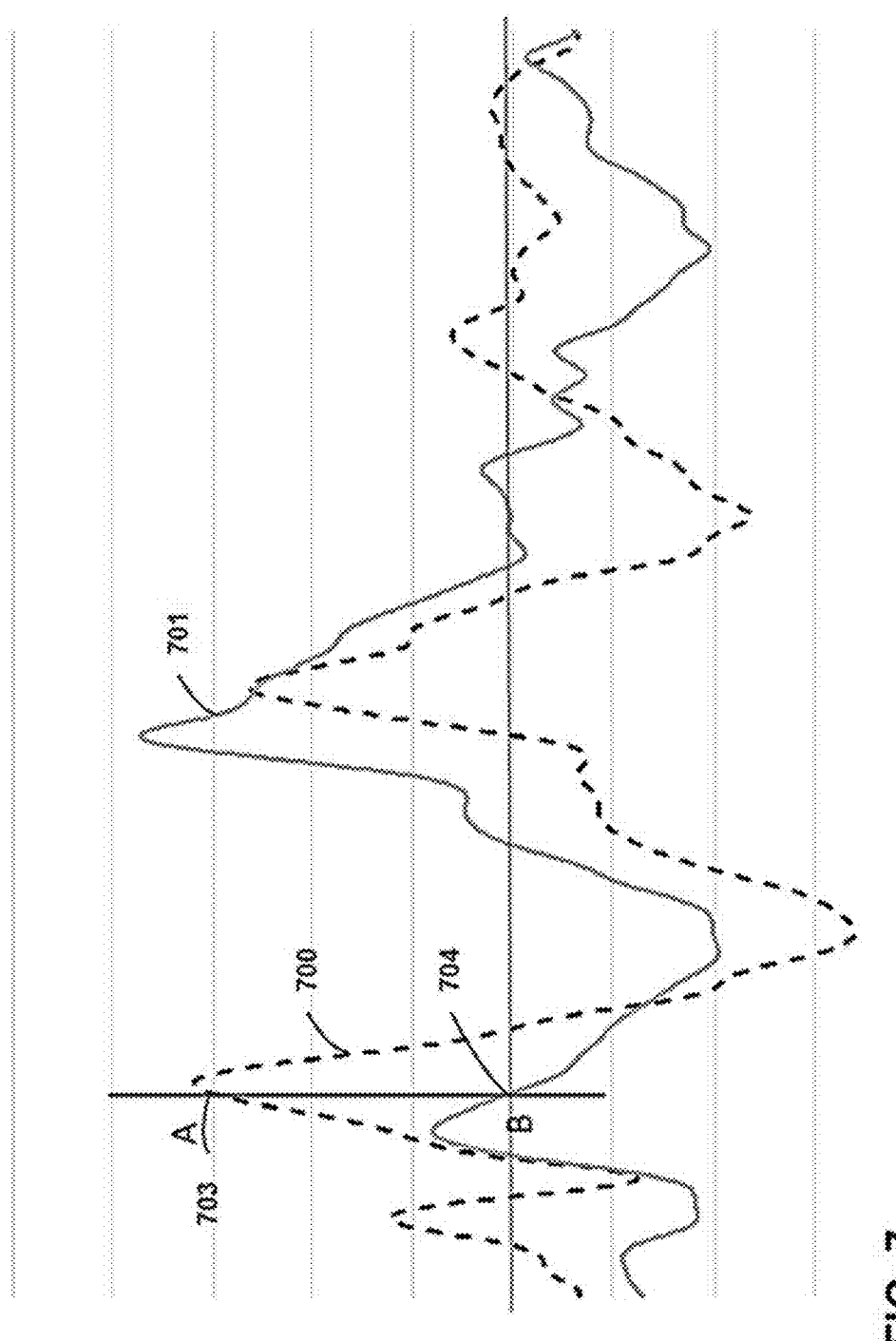
FIG. 7 is an illustration of an example two data samples for a HeadPulse recording.
Figure 8:
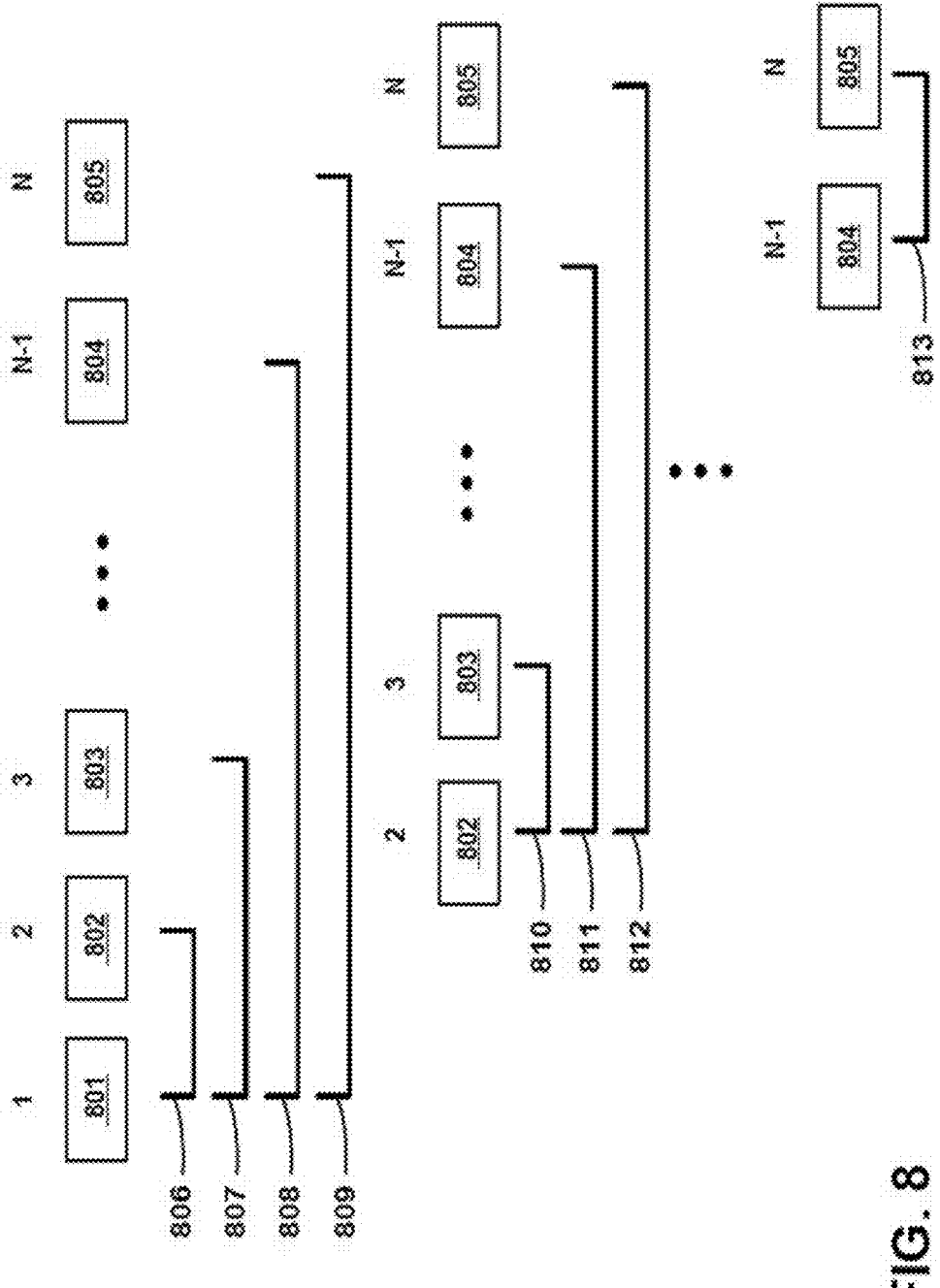
FIG. 8 is an illustration of examples of data samples representing all the HeadPulse recording data samples.

FIG. 7 through FIG. 11 are illustrations of examples of evaluating the data samples of HeadPulse recordings. FIG. 7 is an illustration of an example two data samples 700, 701 for a HeadPulse recording. For the examples herein, the HeadPulse recording consists of a time series of acceleration values covering many heartbeat intervals and all measured axes. The HeadPulse recording data are parsed into R-R intervals associated with the subject's heartbeat. Each heartbeat interval is resampled to include 2048 data points thus making all R-R intervals equal. Each heartbeat interval is called a data sample. The RMS difference between two data samples 700 and 701 is calculated one data point at a time by subtracting a first data point A 703 on the first data sample 700 from a second data point B 704 on the second data sample 701 and squaring the calculated difference, adding all 2048 such data point differences, dividing the total by 2048 and taking the square root. RMS chaos numerical value is calculated from a HeadPulse recording consisting of N data samples. Every data sample, for each axis separately, is calculated against all other data samples for a total of $N(N-1)/2$ data sample pairs as shown in FIG. 8.

FIG. 8 is an illustration of examples of data samples 801-805 representing all the data samples from an entire HeadPulse recording as shown in FIG. 7. Calculations 806-809 are made between the first data sample and all remaining data samples. Calculations 810-812 are made between the second data sample and all remaining data samples. Calculation 813 is made between the second to last data sample 804 and the final data sample 805. Each of these N(N−1)/2 results are squared, averaged and the square root calculated to yield the RMS chaos numerical value for each axis.

Another example of a technique for determining chaos includes a distribution outside the standard deviation calculation. The standard deviation of a data sample is calculated data point by data point using the value of each data sample at that data point. The series of such data points is a curve consisting of 2048 data points both greater than and less than the mean curve. FIG. 4 shows several HeadPulse recordings parsed into multiple data samples and plotted together with the mean 404 and 413 shown and one standard deviation above 405 and 415 and one standard deviation below 403 and 412. On each data sample the number of data points that fall outside of one standard deviation can be tallied.

Figure 9:
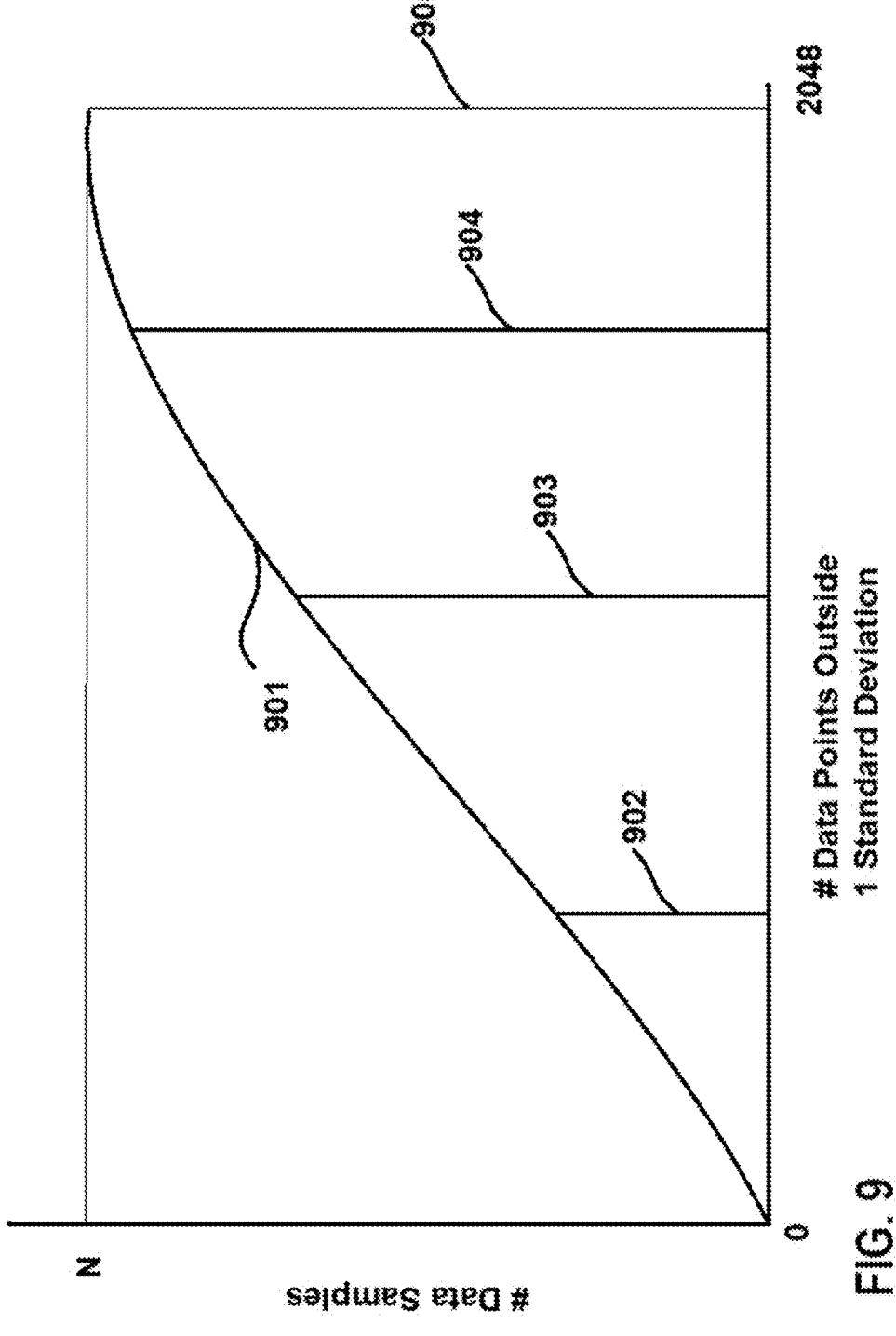
FIG. 9 shows the resulting graph of the number of data samples on the y-axis and the number of data points outside one standard deviation on the x-axis.

FIG. 9 shows the resulting graph 901 of the number of data samples on the y-axis and the number of data points outside one standard deviation on the x-axis. This is calculated for each recorded acceleration axis. The ratio of the value at the $3^{th}$ quarter 904 divided by the value at the $1^{st}$ quarter 902 is a chaos numerical value. Other ratios derived from this plot may also be made including using the values of 902-905 without ratios or with other portions of the graph 901 used for numerical values.

Figure 10:
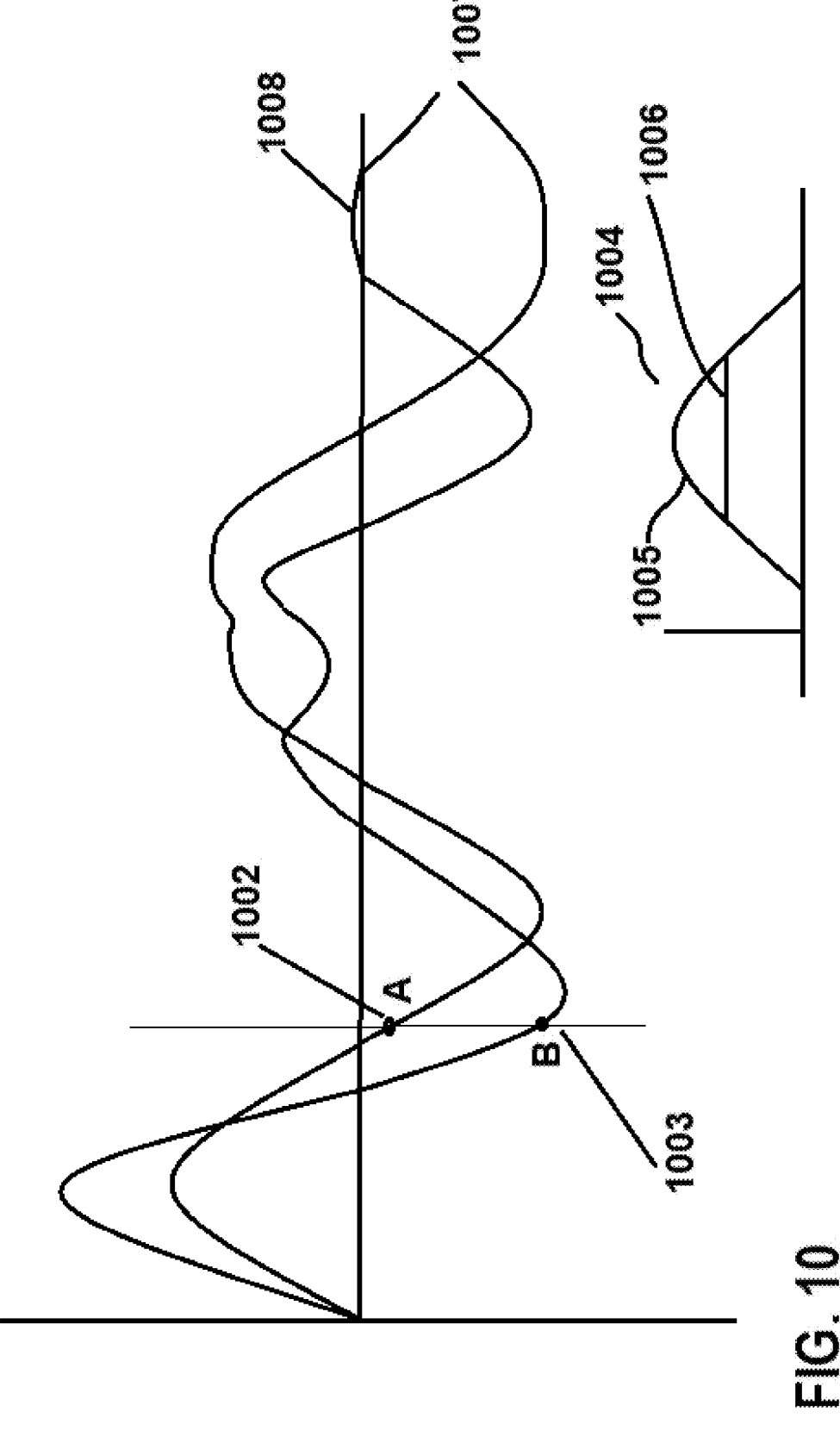
FIG. 10 shows the graph of mean of the data samples from a HeadPulse recording and one of the data samples.

Quartile distribution is another example of a technique for determining chaos. FIG. 10 shows the graph of the mean 1000 of the data samples from a HeadPulse recording and one of the data samples 1001. Quartile distribution is calculated between the mean 1000 and one of the data samples 1001 one data point at a time for each quartile by subtracting data point A 1002 from data point B 1003 and squaring the calculated difference. A histogram of the distribution 1004 of the squared differences for each quartile is created. Each histogram is subjected to a normal distribution fit 1005 resulting in a single numerical value, the histogram width 1006. This result, the width of the normal distribution 1006 is used as a chaos value and several ratio values are also calculated. These include the average of the $2^{nd}$ and $3^{th}$ quartile values divided by the $1^{st}$ st quartile value, the $2^{nd}$ quartile value divided by the $1^{st}$ quartile value, the average of the $2^{nd}$, $3^{th}$ and $4^{th}$ quartile value divided by the $1^{st}$ quartile value and the average of the $1^{st}$ and $2^{nd}$ quartile value divided by the average of the $3^{th}$ and $4^{th}$ quartile value. These calculations are made for each axis. The use of quartile values may be replaced with other divisions that distinguish between the chaos of the data samples at the beginning of the data sample interval and the middle and end of the data sample interval.

Figure 11:
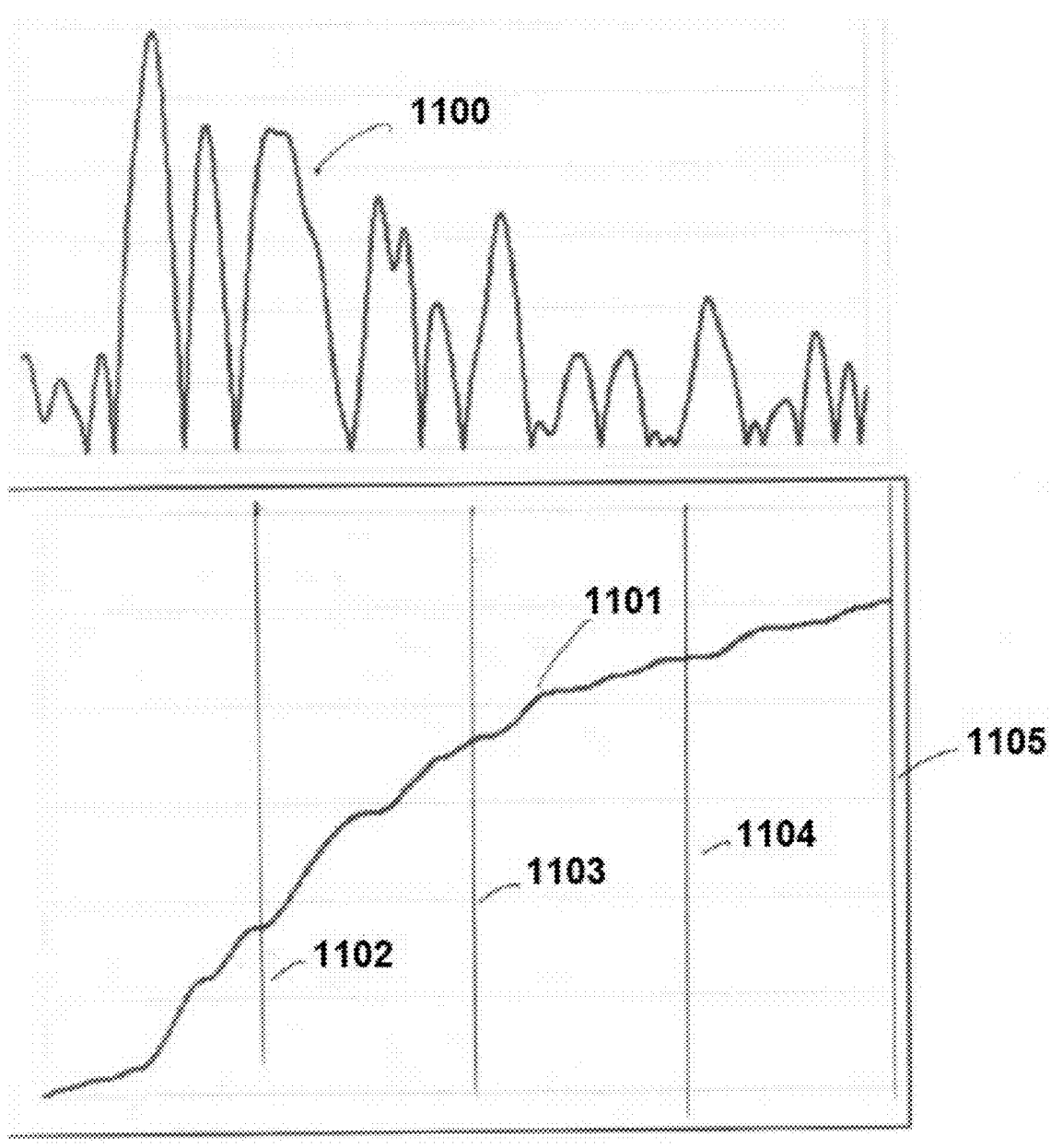
FIG. 11 shows a graph of the absolute value of the mean of the data samples of a HeadPulse recording and its integral.

Integrated mean acceleration is yet another example of a technique for determining chaos. FIG. 11 shows a graph 1100 of the absolute value of the mean of the data samples of a HeadPulse recording. The graph 1101 is the integral of 1100. Each of the quartile values 1102-1105 are used in ratio to determine chaos numerical values. These include the average of the $2^{nd}$ and $3^{th}$ quartile values divided by the $1^{st}$ quartile value, the $2^{nd}$ quartile value divided by the $1^{st}$ st quartile value, the average of the $2^{nd}$, $3^{th}$ and $4^{th}$ quartile value divided by the $1^{st}$ quartile value and the average of the $1^{st}$ and $2^{nd}$ quartile value divided by the average of the $3^{th}$ and $4^{th}$ quartile value. These calculations are made for each axis. The use of quartile values may be replaced with other divisions that distinguish between the chaos of the data samples at the beginning of the data sample interval and the middle and end of the data sample interval.

Figure 12:
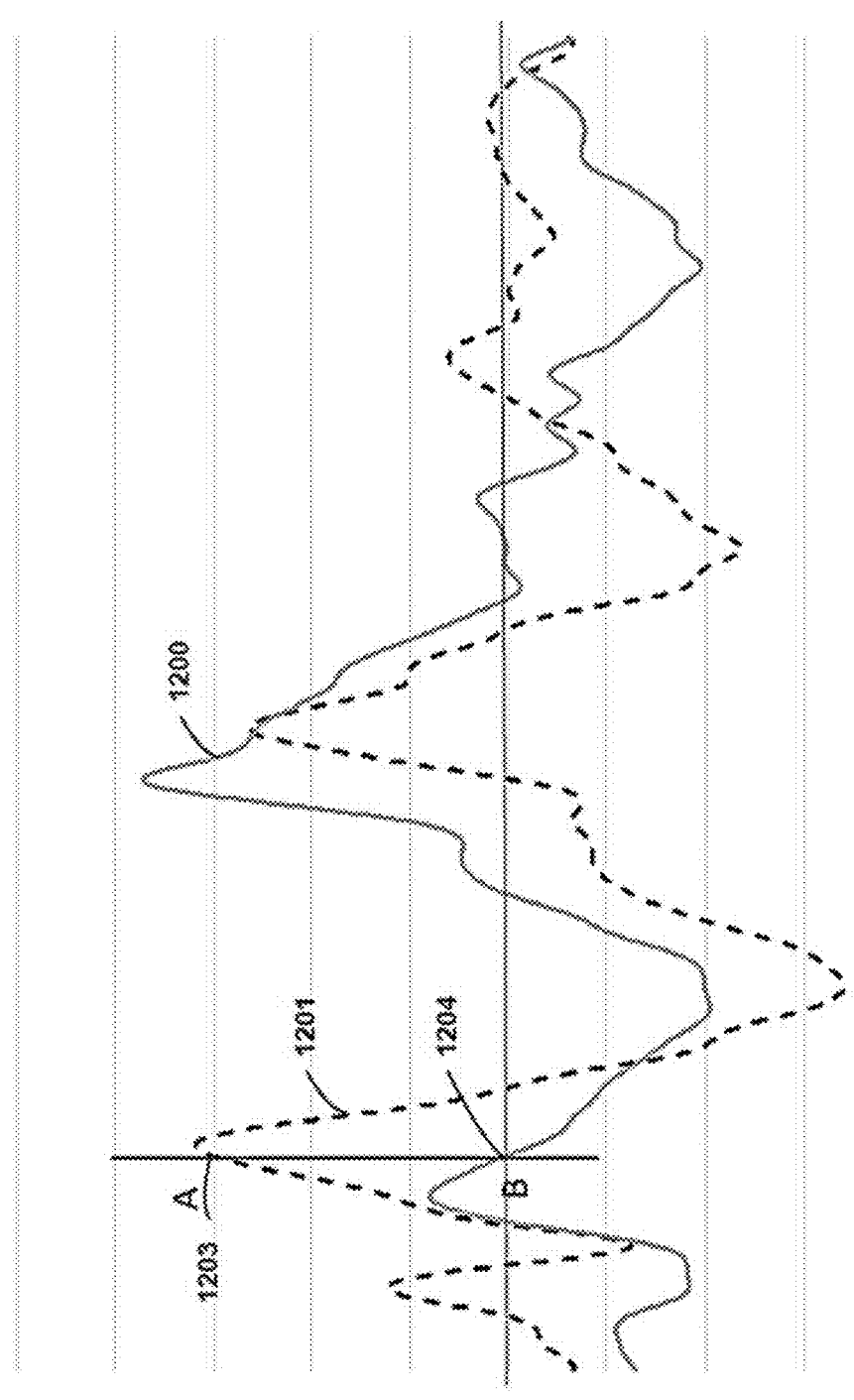
FIG. 12 shows a graph of a data sample and the mean of an entire set of data samples from a HeadPulse recording.

RMS mean chaos is an example of another technique for determining chaos. FIG. 12 shows RMS difference between a data samples 1200 and the mean of all data sample in the same HeadPulse recording 1201 is calculated one data point at a time by subtracting, for example, data point A 1203 from data point B 1204 and squaring the calculated difference, adding all 2048 such data point differences, dividing the total by 2048 and taking the square root. RMS chaos for a HeadPulse recording consisting of the RMS value of N data samples each compared to the mean 1201.

The techniques, devices, and systems discussed above provide several advantages over conventional systems for diagnosing strokes in patients. Patients with LVO stroke (ca. 40% of all ischemic stroke) benefit from rapid removal of the blood clot that has closed their cerebral artery (thrombectomy). The sooner this is performed the better the patient outcome. Conventional techniques require brain imaging with CT or MRI to determine if a patient is suffering from a stroke since clinical examination of the patient alone is not sufficiently accurate. In some cases, the clinical assessment is incorrect to conclude an LVO condition exists because some non-LVO stroke (small vessel stroke) may mimic LVO stroke, and some non-stroke conditions like migraine and seizure may mimic LVO stroke.

As a result, the techniques described above allow for improved diagnoses. The diagnosis of stroke due to LVO is an example of one such diagnosis. A device operating in accordance with the examples above makes the diagnosis more accurate by combining clinical exam features and the acceleration recordings to better identify patients with LVO. A relatively inexpensive portable device can provide accurate diagnoses quickly. Such a device can be used in the emergency setting (prehospital by paramedics, emergency departments at primary stroke centers, on inpatients with sudden change in neurological status) to expedite triage and improve outcomes for this form of stroke. The techniques can be used to detect LVO stroke without use of cross-sectional brain imaging. In addition, use of one or more 3-axis sensors in a single location, or more than one location on the head provides a simple device that can be easily and rapidly applied to the patient without lifting the patients head. The simple nature of the device will allow its use regardless of other interventions. Further, a portable, non-invasive, non-significant risk device in accordance with examples above can determine the presence of stroke within 30-60 seconds. Manufacturing costs of such devices will be orders of magnitude lower than CT and MRI scanning equipment. Furthermore, such devices have no risk of harm to the patient compared to the current state of the art. For example, CT produces radiation exposure and risks renal failure from contrast administration, and MRI risks injury from strong magnetic fields that make MRI contraindicated for patients that have metal implants. Also, such devices can be used at the bedside (runs on batteries) anywhere inclusive of out of hospital locations and in hospital locations.

In typical situations, medical professionals are trained in use of the headset and understand the utility of using this prediction tool to aid in the diagnosis of LVO. Individuals using the device are trained using specific instructions for use. The system can be used in an ambulance, a hospital, or other location. In most situations, the device is stored in a sealed container. The headset may have an internal, electronic serial number which may also be embossed on the device externally. When a patient with a suspected stroke is identified, the device user removes the headset from its packing, turns it on by switch or pulling an insulative tab thus engaging a battery. The headset is then placed in the coronal plane on the subject.

For some examples where the headset includes an LED user interface and the analyzer is within a computer, the device user attaches a PPG device to the patient's earlobe, finger, or other extremity, plugs the PPG sensor wire into the headset, and confirms proper operation of PPG by observing an LED flash with each heartbeat. In addition, or in unison, the user places an ECG electrode on each shoulder or upper limb of the patient and connects the ECG electrodes to the headset device through a plug connector. This provides an electrical pulse to the device every time the heart beats which can be observed by the user through another flashing LED.

After sufficient HeadPulses have been recorded, the device illuminates a particular colored LED to let the user know the data is complete. Poor quality recording is indicated by another LED. In response, the user repositions the headset, replaces the headset, or engages methods to calm the patient to allow sufficient recording to avoid degradation by gross movements of the head.

Following acquisition of sufficient HeadPulse recording, the user obtains a focused neurological examination of the patient, and enters these findings on an attached computer, or computer communicating with the device wirelessly. The analyzer in the attached computer executes the algorithm and provides an electronic message that reports the degree of certainty that the patient is or is not having an LVO stroke. The user then uses this information to make the decision on the next steps of care. This information can be transmitted to a receiving hospital, to medical consultants, or to other personnel involved in the emergency care of the patient via text, e-mail, website, or other direct service.

In examples where the analyzer is implemented within the headset, the clinical examination information can be entered into the headset via wired, wireless or physical switches and an internal microprocessor inside the headset executes the algorithm and displays the results on an output user device such as visual display on the headset LED arrangement.

The techniques, devices, and systems discussed herein, aids in the diagnosis of LVO stroke and helps in triage decisions that will improve the outcomes of patients with LVO stroke by shortening the time to effective treatment.

HeadPulse measurements from 42 subjects with suspected stroke who had CTA performed in a major medical center were obtained and analyzed {Smith, et al. ISC 2019}. Analysis of waveforms from subjects without LVO revealed close temporal linkage of each data sample and close temporal similarity between each data sample. Data samples from LVO stroke patients were not closely coupled with the heartbeat and appear "chaotic". Chaos was objectified with a series of statistics and submitted to a machine learning algorithm along with components of the NIH Stroke Scale to derive a predictive model of LVO. Subjects with LVO had chaos significantly more frequently than subject without LVO (83% vs. 25%, p=0.0002). When combining this model with simple features of the neurological (asymmetry in upper limb strength), 100% of LVO patients were properly categorized (Keenan et al., ISC 2019).

The combination of upper limb strength asymmetry plus data from the HeadPulse recordings can be an effective tool to determine the presence of LVO using a portable system that requires only 30-60 seconds using a headset that contains the electronic components to measure the HeadPulse and computers programmed with the model algorithm.

As mentioned above, the techniques discussed herein may be adapted for use with other conditions. For example, the HeadPulse contains information relevant for concussion and traumatic brain injury (TBI). Frequency analysis of the HeadPulse shows a shift of the component frequencies of brain forces during the heartbeat to higher harmonics of the baseline heart rate. This frequency shift indicates that the skull and brain are vibrating at a higher frequency than normal during a period following concussion and TBI. Normal subjects without concussion or TBI do not have significant energy in the range of 6 or higher harmonics of their heart rate, while more than 86% of those with concussion do, allowing for an objective biometric of concussion and TBI. Use of this biometric will help determine when it is safe to return an athlete to play, or return a soldier to battle, as the brain is vulnerable during this phase of concussion recovery. The biometric data indicates that the HeadPulse is abnormal beyond the time the subject feels well. Since feeling well (a subjective measure) is the gold-standard for returning to play, use of this objective biometric information will help reduce the frequency of second impact syndrome and perhaps chronic traumatic encephalopathy. Using the HeadPulse to determine the etiology of altered mental status in patients who arrive without a clinical history to a clinic or emergency department will be helpful to identify patents that have had some form of head trauma.

Analysis of HeadPulse data will allow the discrimination of intracerebral hemorrhage from LVO stroke. Analysis of HeadPulse data from subjects with suspected stroke, without LVO but with ICH, do not have the chaos signature of LVO. Discrimination of ICH from LVO is important, as ICH patients may not need triage to specialty centers while LVO patients need rapid intervention.

Use of more than one accelerometer at orthogonal relationship (X-Y-Z axis) provides additional information about the HeadPulse in various disease states. Concussion is particularly seen in lateral sensors, and LVO in vertical sensors. Use of bilateral 3-axis accelerometers allows for the detection of the heartbeat. This takes advantage of scalp plethysmography where the scalp swells centripetally during systole. Disparity in opposite direction forces derived from two or more sensors mounted on opposite sides of the skull provides a waveform coupled to the heartbeat. This derived trigger is used to parse the HeadPulse recording into data samples. Signal averaging the data samples allows amplitude, phase and frequency analysis.

The amplitude of the data sample's principle peak in each axis is modulated by respiration. Respiration can be deduced from this signal. This signal can be further improved by combining the signal for each axis. The heart rate, R-R interval, also varies with respiration. These signal measurements can be combined to provide a stable and accurate respiration signal.

The HeadPulse measurement device can be implemented using a MEMS chip, digitizer, battery and RF or infrared transmitter. These components can be integrated into one or two semiconductor ASICs. The sensor chips are typical of those found in smart phones and measure less than 2 mm square and less than 1 mm thick. At these dimensions, the entire device can be embedded in the temple arms of glasses, as part of a hearing aid, as a patch attached with adhesive or injected as a capsule under the skin. The advantage of having a non-intrusive device embedded in one or more devices that are nearly always monitoring is that when a neurological event occurs, it is detected within a few seconds. To capture the data necessary to glean the signature for many neurological events of clinical interest significant data will be necessary before and after the event. With conventional clinical trials obtaining such data would be economically infeasible. With a very low-cost embedded device the data could be obtained nearly continuously from a vast number of patients at extremely low costs. Many strokes occur during sleep, known as "wake up strokes." If a continuous monitor could alert the patient or the patient's caregiver that a stroke is occurring, outcomes will be improved.

Additional information is provided from static accelerometers with respect to head position at the time the signal is obtained. The polarity of the accelerometers is known relative to the headset in which they are housed. Assuming the headset is worn in a particular direction on the head (typically coronally) the position of the head relative to gravity is known. This information can be integrated into the algorithm to refine its predictive value for various brain diseases. In addition, geomagnetic sensors can be integrated into the device to provide additional information of body and headset orientation.

A GPS device can be integrated into the headset to provide earth surface location of the device. This will be used to determine patient location and via cellular technology will transmit the GPS coordinates periodically to provide a mapping function to the end-user. This will provide real time information about patient location to treating physicians to improve their efficiency in managing patient care.

Accelerometers lose sensitivity in the low frequency range. In order to increase this sensitivity at lower frequencies, a novel device can be created. A liquid filled sphere will oscillate if perturbed by an outside force or vibration and this oscillation can be measured by either reflected or refracted light off of the surface of the sphere. For a refracted ray of light entering the sphere off axis the ray is first refracted upon entering the sphere, is then reflected off of the rear surface and is again refracted leaving the sphere. The position and angle of the exiting light is a highly sensitive measure of the spheres shape. Light sources such as a laser can be highly collimated and offer a perfect probe source for measuring the liquid filled sphere. Measuring the returning light beam over time will give a time resolved motion of the liquid filled sphere sensor. Measuring at three orthogonal angles will give a time resolved characterization of the motion of the liquid filled sphere sensor and hence the motion of any object in contact with the liquid filled sphere sensor.

Clearly, other embodiments and modifications of this invention will occur readily to those of ordinary skill in the art in view of these teachings. The above description is illustrative and not restrictive. This invention is to be limited only by the following claims, which include all such embodiments and modifications when viewed in conjunction with the above specification and accompanying drawings. The scope of the invention should, therefore, be determined not with reference to the above description, but instead should be determined with reference to the appended claims along with their full scope of equivalents.

What is claimed is:

1. A system comprising:
a headset, the headset housing a three-dimensional accelerometer configured to generate three orthogonal signals, each orthogonal signal indicative of acceleration in an axis orthogonal to two other axes of a motion of the three-dimensional accelerometer due to head movement in a brain due to heartbeat;
an analyzer having an input configured to receive a plurality of data samples based on each orthogonal accelerometer signal, each data sample indicative of the head movement associated with a different heartbeat in a single axis, the analyzer configured to determine a level of chaos of the plurality of data samples and indicate that a large vessel occlusion (LVO) has occurred in the brain when the level of chaos exceeds a threshold,
wherein the level of chaos is at least partially based on a difference between signal levels at a plurality of selected times of each of a plurality of acceleration versus time functions of the plurality of data samples,
wherein the level of chaos is at least partially based on a calculation of the plurality of acceleration versus time functions, and
wherein the calculation comprises determining a difference function for each data sample at a plurality of times, each difference function comprising a difference between the data sample and an average of all data samples.

2. The system in accordance with claim 1, wherein the calculation further comprises:
rectifying and summing each difference function to generate a plurality of results;
summing the plurality of results to generate a sum of results; and
normalizing the sum of results to a number of data samples or normalizing the sum of results to a minimum and a maximum of the average of data samples at a plurality of time points.

3. The system in accordance with claim 1, wherein the calculation comprises:
determining a root-mean-square of the difference function.

4. The system in accordance with claim 3, wherein the calculation further comprises:
summing the root-mean-square of the difference function to generate a sum; and normalizing the sum to a minimum and a maximum of the average of the data samples at a plurality of time points.

5. The system in accordance with claim 1, wherein the calculation comprises:
applying a cross-correlation function to each data sample of the plurality of data samples to an average of all data samples of the plurality of data samples; or
determining a number of times of the plurality of times that differ from an average.

6. The system in accordance with claim 1, wherein the processor is configured to determine the level of chaos at least partially based on a shape of an acceleration versus time function of each data sample of the plurality of data samples.

7. The system in accordance with claim 1, wherein the analyzer is configured to time align the plurality of the acceleration versus time functions based on information from the plurality of the acceleration versus time functions.

8. The system in accordance with claim 1, wherein the analyzer is configured to time align the plurality of the acceleration versus time functions, at least partially, from an electrocardiogram (ECG) or photoplethysmograph (PPG) signal indicative of cardiac contractions.

9. The system in accordance with claim 1, further comprising:
a transmitter configured to transmit a wireless signal indicative of the plurality of data samples; and
a receiver configured to receive the wireless signal and provide the plurality of data samples to the analyzer.

10. The system in accordance with claim 9, further comprising:

an analog to digital converter (ADC) configured to sample each orthogonal accelerometer signal to generate the plurality of data samples.

11. The system in accordance with claim 10, further comprising:

a controller configured to time align the plurality of data samples before transmission of the wireless signal comprising time aligned data samples.

12. The system of claim 1, wherein the headset further comprises the analyzer.

* * * * *